(12) United States Patent
Sturrock et al.

(10) Patent No.: US 7,951,834 B2
(45) Date of Patent: May 31, 2011

(54) ANGIOTENSIN I-CONVERTING ENZYME (ACE) INHIBITORS

(75) Inventors: Edward Sturrock, Cape Town (ZA); Aloysius Nchinda, Cape Town (ZA); Kelly Chibale, Claremont (ZA)

(73) Assignee: University of Cape Town, Cape Town (ZA)

( * ) Notice: Subject to any disclaimer, the term of this patent is extended or adjusted under 35 U.S.C. 154(b) by 594 days.

(21) Appl. No.: 11/921,110

(22) PCT Filed: May 29, 2006

(86) PCT No.: PCT/IB2006/001394
§ 371 (c)(1),
(2), (4) Date: Nov. 27, 2007

(87) PCT Pub. No.: WO2006/126086
PCT Pub. Date: Nov. 30, 2006

(65) Prior Publication Data
US 2009/0281160 A1     Nov. 12, 2009

(30) Foreign Application Priority Data

May 27, 2005    (ZA) .................................. 2005/04366

(51) Int. Cl.
*A61K 31/404* (2006.01)
*C07D 209/20* (2006.01)
(52) U.S. Cl. ........................................ 514/419; 548/494
(58) Field of Classification Search ........................ None
See application file for complete search history.

(56) References Cited

OTHER PUBLICATIONS

Almquist R. G et al., "Synthesis and Biological Activity of the Ketomethylene Analogue of a Tripeptide Inhibitor of Angiotensin Convening Enzyme." Journal of Medicinal and Pharmaceutical Chemistry, American Cancer Society, vol. 23, No. 12, pp. 1392-1398, 1980.
Blaksjaer, P. et al., "Sml2 reduced Thioesters as Synthons of Unstable Acyl Radicals: Direct Synthesis of Potential Protease Inhibitors via Intermolecular Radical Addition." Journal of the American Chemical Society, vol. 125, No. 14, pp. 4030-4031, 2003.
Ewenson, A. et al., "Synthesis of Ketomethylene and Dehydroketamethylene Pseudo-Dipeplides," International Journal of Peptide and Protein Research, International Journal of Peptide and Protein Research, vol. 31, No. 3, pp. 269-280, 1988.
Ewenson, A et al., "Ketomethylene Pseudopeptide Analogues of Substance P Synthesis and Biological Activity" Journal of Medicinal Chemistry, vol. 29, No. 2, pp. 295-298, 1986.
Lygo, B et ai., "Synthesis of Xaa-Gly-Xaa' Keto-Methylene Tri-Peptide Isosteres Incorporating Phenylalanine, Tyrosine and Valine Units," Tetrahedron Letters, vol. 36, No. 20, pp. 3577-3580, 1995.
Meyer, R.F et al, "Novel Synthesis of (S)-1-[5-(benzoylamino)-1, 4-dioxo-6-phenyl hexyl]-L Proline and Analogues Potent Angiotensin Convening Enzyme Inhibitors," Journal of Medicinal Chemistry, American Chemical Society, vol. 24, No. 6, pp. 964-969, 1981.
Nchinda et al., "Synthesis of Novel Keto-ACE Analogues as Domain-Selective Angiotensin I-Converling Enzyme Inhibitors," Bioorganic & Medicinal Chemistry Letters, vol. 16, No. 17, pp. 4612-4615, 2006.
Redelinghuys, P. et al., "Novel Ketomethylene Inhibtlors of Angiotensin I-Converting Enzyme (ACE) Inhibition and Molecular Modelling," Biological Chemistry, vol. 387, No. 4. pp. 461-466, 2006.
Vabeno, J. et al,, "Dipeplidornimetic Ketomethylene Isosteres as Pro-Moieties for Drug Transport via the Human Intestinal Di-/Tripeptide Transporter hPEPT1 Design, Synthesis, Stability, and Biological Investigations," Journal of Medicinal Chemistry, vol. 47, No. 19, pp. 4755-4765, 2004.
Vabeno, J et al , "Diastereoselective Reduction of a Chiral N-Boc-Protected Delta-Amino-Alpha, Beta-Unsaturated Gamma-Kelo Ester Phe-Gly Dipeptidomimetio," Journal of Organic Chemistry, vol. 67, No. 26, pp. 9186-9191, 2002.
Vabeno, J. et al , "Phe-Gly Dipeptidomimetics Designed for the Di-/Tripeptide Transporters PEPT1 and PEPT2 Synthesis and Biological Investigations," Journal of Medicinal Chemistry, vol, 47, No. 4, pp. 1060-1069, 2004.

*Primary Examiner* — Yong Chu
*Assistant Examiner* — Michael Barker
(74) *Attorney, Agent, or Firm* — Kilpatrick Townsend & Stockton LLP

(57) ABSTRACT

This invention relates to a process for the synthesis of ketomethylene derivatives of the tripeptide Phe-Gly-Pro ("keto-ACE", compound 5a) and analogues thereof. The synthesis process proceeds via an $\alpha,\beta$-unsaturated keto intermediate. A key feature of the process involves a Horner-Emmons olefination of the, -unsaturated keto-phosphonate with ethyl glyoxylate. Keto-ACE analogues produced by the process of the invention display C-domain selectivity.

3 Claims, 2 Drawing Sheets

ANGIOTENSIN I-CONVERTING ENZYME (ACE) INHIBITORS

BACKGROUND OF THE INVENTION

Angiotensin I-converting enzyme (ACE; EC 3.4.15.1) is a zinc-dipeptidyl carboxypeptidase that plays a key role in blood pressure regulation by converting the inactive decapeptide angiotensin I to the potent vasopressor octapeptide angiotensin II by cleavage of the carboxy-terminal dipeptide.[1] It also inactivates the vasodepressor nonapeptide bradykinin.[2,3] Thus, the inhibition of ACE has become a primary strategy in the treatment of hypertension, myocardial infarction, heart failure, and diabetic nephropathy.[4] There are a number of commercially available ACE inhibitors, including captopril,[5,6] lisinopril, and enalapril, which have established themselves in the therapy of hypertension and congestive heart failure.[7,8] However, undesirable side effects such as persistent cough, loss of taste, and angioedema have been associated with current-generation ACE inhibitors.[9,10] Therefore, the development of novel effective drugs for the treatment of hypertension and cardiovascular diseases still remains an important goal. The recent availability of the crystal structure of the testis ACE-lisinopril complex has opened the possibility of structure-guided design of second-generation, domain-selective ACE inhibitors.[11]

SUMMARY OF THE INVENTION

Figure 1:
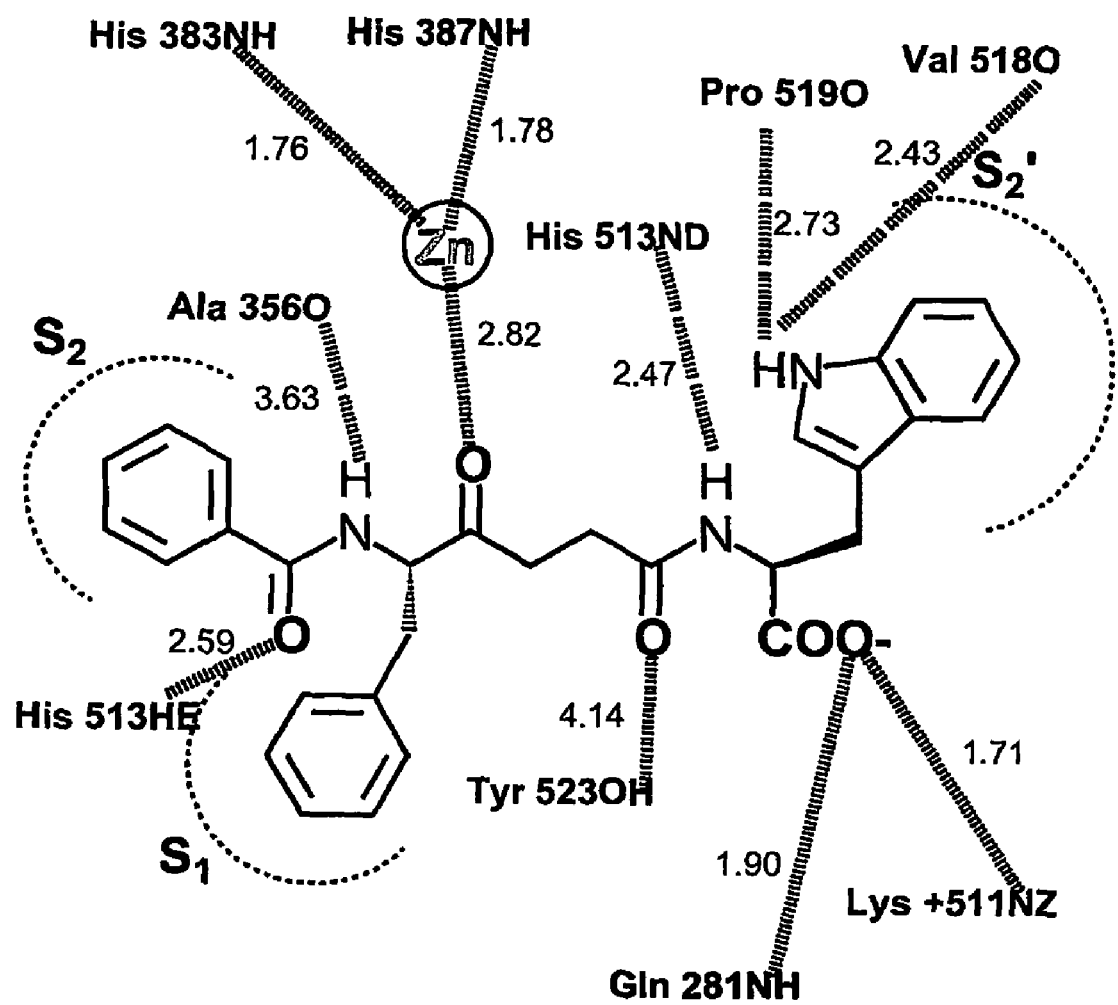
FIG. 1 shows a schematic representation of the principal hydrogen bonding interactions between compound 5b prepared according to the invention and the active site residues of ACE.

According to a first embodiment of the invention, there is provided a process for the synthesis of a ketomethylene derivative of the tripeptide Phe-Gly-Pro ("keto-ACE", compound 5a) and analogues thereof, wherein the synthesis process proceeds via an α,β-unsaturated keto intermediate.

The α,β-unsaturated keto intermediate may be a benzoyl keto intermediate such as Ethyl (E/Z)-(5S)-5-[(N-benzoyl) amino]4-oxo-6-phenyl-2-hexenoate; or a Boc keto intermediate such as ethyl-(E/Z)-(5S)-6-phenyl-5-[(tert-butyloxycarbonyl)amino]-4-oxo-2-hexenoate.

A methyl ester, typically a phenyl alanine methyl ester, may be used as a starting material in the process. The methyl ester may be converted to β-keto phosphonate, which may then be converted to the intermediate α,β-unsaturated keto derivative by Horner-Emmons olefination, typically in the presence of ethyl glyoxylate.

The intermediate α,β-unsaturated keto derivative may then be hydrogenated to give an intermediate ketomethylene ester derivative. This ester may be hydrolysed to provide a desired add. The acid may be peptide coupled with a corresponding O-protected amino acid to form corresponding ester compounds. These compounds may be catalytically hydrogenated or saponified to form the desired ketomethylene derivative.

The methyl ester may be a benzoyl methyl ester such as N-Benzoyl-methyl ester.

Alternatively, the methyl ester may be a Boc methyl ester such as N-Boc-L-phenylalanine methyl ester.

According to a second embodiment of the invention, there is provided a keto-methylene derivative prepared by the process described above.

According to a third embodiment of the invention, there is provided new ACE inhibitors which are symmetric and asymmetric peptidomimetics, preferably the heptapeptide, with P2, P1, P1' and P2' groups where P2 is absent or is aminobenzoyl, P1 is Phe, P1' is Ala, Trp, Arg or Lys, ethyl or butyl or tertiary-butyl, and P2' is Trp or Phe, or analogues thereof. The peptidomimetic may be a ketone, carboxylate, hydroxamate, boronate, phosphonate, phosphoramide, guanidinium, sulfate, vanidate, silanol or silanediols, preferably a ketone. A new compound selected from the group consisting of (5S)-5-[(N-benzoyl)amino]-4-oxo-6-phenyl-hexanoyl-L-tryptophan; (5S)-5-[(N-benzoyl)amino]-4-oxo-6-phenyl-hexanoyl-L-phenylalanine; (5S)-6-phenyl-5-[(tert-butyloxycarbonyl)-amino]-4-oxo-hexanoyl-L-proline; (5S)-6-phenyl-5-[(tert-butyloxycarbonyl)-amino]-4-oxo-hexanoyl-L-tryptophan; and (5S)-6-phenyl-5-[(tert-butyloxycarbonyl)-amino]-4-oxo-hexanoyl-L-phenylalanine, and analogues thereof.

According to a fourth embodiment of the invention there is provided a pharmaceutical composition including a compound described above. The composition may be used for the treatment of hypertension and/or cardiovascular disease.

DETAILED DESCRIPTION OF THE INVENTION

The synthesis of novel analogues of the ketomethylene isostere keto-ACE[12-14], molecular docking, and inhibition constants for these compounds are described herein.

ACE is a complex two-domain enzyme, comprising an N and a C domain, each containing an active site with similar but distinct substrate specificities and chloride-activation requirements. The N- and C-domain sites of ACE hydrolyze angiotensin 1 (Ang I) and bradykinin (BK) at comparable rates in vitro, but in vivo it appears that the C-domain is primarily responsible for regulating blood pressure. This might suggest that a C-selective inhibitor would have a profile comparable to current mixed inhibitors, but this is not necessarily the case.

First, while Ang I is hydrolyzed predominantly by the C domain in vivo, BK is hydrolyzed by both domains and therefore selective inhibition of the C-domain site will allow some level of BK degradation to continue, catalyzed by the N-domain. This could be sufficient to prevent the excessive BK accumulation that has been observed during attacks of angioedema. Second, BK potentiation by $B_2$ receptor resensitization is maximal when both the N- and C-domains are inhibited, suggesting that a pure C-selective inhibitor will have a lower propensity for excessive BK stimulation. Third, the multiple Ang and non-Ang peptides known to be vasoactive are not hydrolyzed equally by the two domains, making it likely that the ratio of vasopressor to vasodilator peptides will differ between C-selective and mixed inhibitors. Thus, a highly selective C-domain inhibitor has the potential for effective blood pressure control with reduced vasodilator-related side effects.

In contrast to a C-selective inhibitor, an N-selective inhibitor may open up novel therapeutic areas. As discussed, the N-domain appears to play a minor role in blood pressure control in vivo. At least three physiologically important peptides are hydrolyzed preferentially or exclusively by the N domain: luteinizing hormone-releasing hormone (LH-RH), $Ang_{(1-7)}$, and AcSDKP (N-acetyl-seryl-aspartyl-lysyl-proline). The contribution of ACE to the metabolism of LH-RH and $Ang_{(1-7)}$ in vivo is unclear, but there is increasing evidence that ACE is the principal metabolizing enzyme for AcSDKP, a natural hemoregulatory hormone. AcSDKP has anti-proliferative and anti-fibrotic activities and may have utility in protecting hematopoietic stem cells against chemotherapy-induced injury and in limiting cardiac fibrosis. Administration of ACE inhibitors results in a 4-6-fold elevation of AcSDKP plasma levels. This may be the basis for the observed association between ACE inhibitors and anemia, and the effective treatment of altitude polycythemia by the ACE inhibitor enelaprilat.

The pattern of keto-ACE (a ketomethylene derivative of the tripeptide Phe-Gly-Pro) inhibition of the hydrolysis of various substrates by somatic ACE indicates that it may be relatively selective for one of the ACE active sites. Deddish et al.[14b] showed that this was indeed the case and that the ketomethylene derivative inhibits the hydrolysis of angiotensin I and bradykinin by the C domain at concentrations 38- to 47-fold lower than by the N domain of somatic ACE.

Ketomethylene dipeptide isosteres have proved particularly useful in the design of efficient peptidomimetic inhibitors,[15-17] and, more specifically, are excellent building blocks for HIV-1 protease inhibitors.[18-21]

To explore the scope of the ketomethylene dipeptide approach and to establish a practical synthetic route with the use of readily available starting material and a convenient experimental work-up, the preparation of keto-ACE was revisited. Several strategies and modifications in the synthesis of keto-ACE have been forwarded,[12-14a] but these synthetic approaches have certain limitations. One of the methods used in the past two decades is the modified Dakin-West reaction,[13] which proceeds via the 5-oxazolone derivative, thus resulting in a racemic mixture. Another method[12,14a] uses a Grignard reagent with 2-pyridyl thiolate, giving the keto acetal intermediate in low yield. In a further study, García-López et al.[22,23] reported the synthesis of ketomethylene dipeptide analogues, which required the use of the carcinogenic and extremely unstable reagent diazomethane. Moreover, a number of parameters in the general synthesis of keto-ACE, such as reaction yields, cost, and reaction conditions, still require optimization.

Synthesis of keto-ACE and Analogues (Scheme 1)

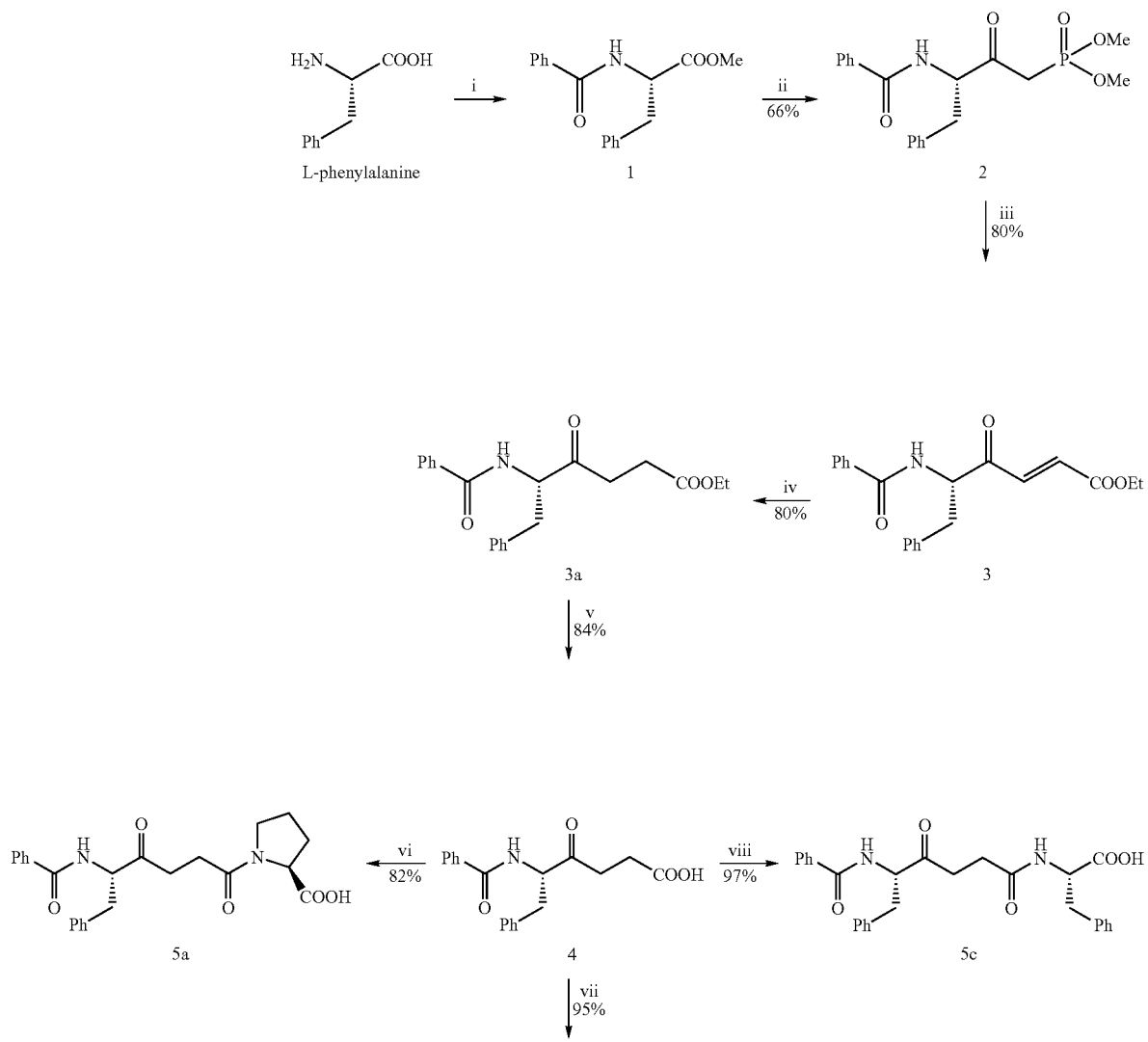

-continued

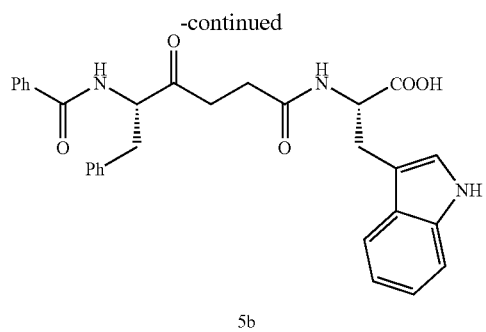

5b

Reagents and conditions:
(i) (a) benzoyl chloride, 1,4-dioxane, 1M NaOH, 0° C., 30 min; (b) SOCl$_2$, dry MeOH, 0° C. to rt, 24 h; (ii) (CH$_3$O)$_2$P(O)CH$_3$, nBuLi, THF, −78° C.; (iii) EtOOCCHO, K$_2$CO$_3$, EtOH, 25° C.; (iv) H$_2$, Pd/C, EtOAc, rt; (v) 0.5N LiOH, THF-MeOH (8:2 ratio), rt; (vi) (a) L-proline benzyl ester hydrochloride, EDC.HCl, HOBt, iPr$_2$NEt (2.0 equiv), DMF/CH$_2$Cl$_2$, rt, 48 h; (b) H$_2$, Pd/C, EtOAc-MeOH (3:1 ratio), rt, for 5a; (vii) (a) L-tryptophan methyl ester, EDC.HCl, HOBt, iPr$_2$NEt (1.0 equiv), DMF/CH$_2$Cl$_2$, rt; (b) 0.5N LiOH, THF-MeOH (8:2 ratio), rt, for 5b and (viii) (a) L-phenylalanine methyl ester hydrochloride, EDC.HCl, HOBt, iPr$_2$NEt (2.0 equiv), DMF/CH$_2$Cl$_2$, rt; (b) 0.5N LiOH, THF-MeOH (8:2 ratio), rt, for 5c.

General Process:

The starting material, N-Benzoyl-methyl ester 1 was prepared from L-(−)-phenylalanine in the presence of benzoyl chloride in 1,4 dioxane and 1 M NaOH solution followed by treatment with thionyl chloride and methanol to give the resulting ester in a quantitative yield. This N-Benzoyl-methyl ester 1 was converted into the β-keto phosphonate 2 by treatment with 8 equivalents of lithiated dimethyl methyl phosphonate in anhydrous THF at −78° C. following the procedure as described by Déziel et al (Scheme 1).[16] The key intermediate α,β-unsaturated keto derivative 3 was obtained in excellent yield by the Horner-Emmons olefination[24] of 2 with one equivalent of freshly prepared ethyl glyoxylate[24], in the presence of one equivalent of potassium carbonate and dry ethanol at ambient temperature. However, it was found that the above reaction conditions gave a substantial amount of the cis-isomer [ratio, 85:15 (trans:cis)] without any racemisation (the ratio of the trans:cis isomer was determined from the $^1$H NMR spectra). Separation of the above isomeric mixture was found to be unnecessary as hydrogenation of the double-bond afforded a single product and thus the mixture was used directly in the next reaction step. The enone mixture of isomers 3 was then hydrogenated over 10% Pd on carbon to give the intermediate ketomethylene ester derivative in 80% yield (Scheme 1). This ester was hydrolysed in the presence of 0.5N-LiOH in THF-MeOH (8:2) at room temperature followed by column chromatographic purification to give the desired acid 4 in 84% yield without any detectable racemization at the stereogenic centre. The spectroscopic data obtained for compound 4 corresponded to those reported by Almquist et al.[12]

Peptide coupling of the free acid 4 with the corresponding O-protected amino acids was effected using EDC.HCl in the presence of HOBt and diisopropyl ethyl amine as a base to provide the corresponding ester products in excellent yields (88% in the case of L-proline benzyl ester hydrochloride, 90% and 92% in the case of L-tryptophan methyl ester and L-phenylalanine methyl ester hydrochloride respectively). The keto-ACE 5a was then obtained in 82% yield by catalytic hydrogenation of the benzyl ester group using 10% Pd on carbon. The spectroscopic data obtained for compound 5a corresponded to those reported by Almquist et al.[12] The methyl esters obtained when using the L-tryptophan methyl ester and L-phenylalanine methyl ester hydrochloride were saponified with aqueous 0.5N LiOH and a mixture of THF-MeOH to afford 5b and 5c in 95% and 97% yield, respectively.

Synthesis of Keto-Ace Analogues Possessing a t-butyl P2 Residue (Scheme 2)

General Process:

The above process was also extended to a more general synthetic procedure (Scheme 2). Tert-butyl ester cleavage of 10 was achieved by treatment with 0.5M triflic acid in methylene chloride at 0° C. for 2 h. This was followed by benzoylation of the free amine with excess benzoyl chloride in dry pyridine for 24 h gave 85% yield of the benzamido derivative followed by hydrogenolysis to afford 5a in 90% yield (Scheme 2). Compound 11a was also obtained in excellent yield.

Scheme 2

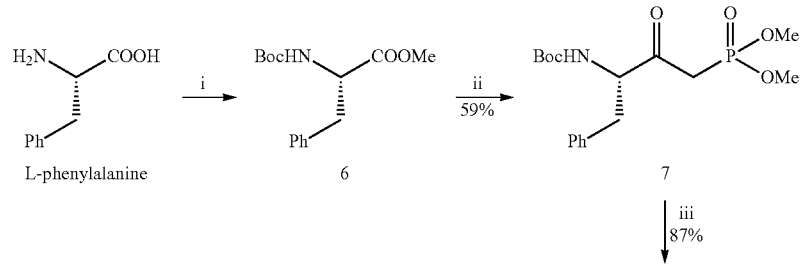

-continued

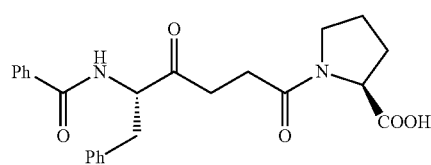
5a

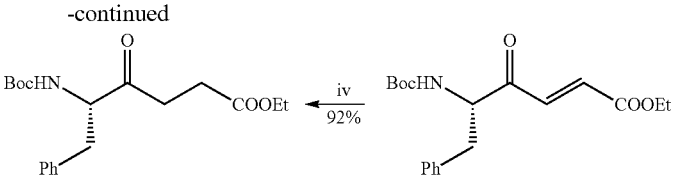
8a      8

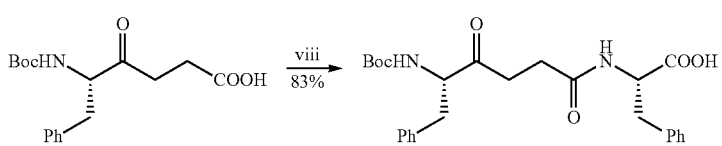
10     9     11c

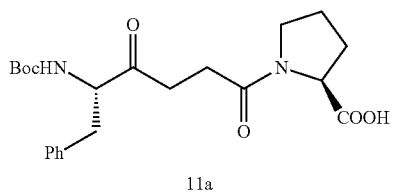
11a

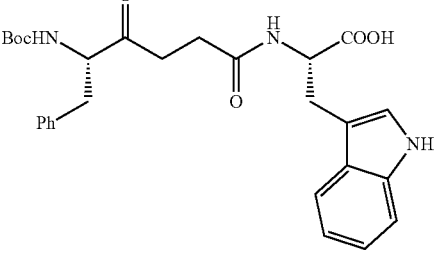
11b

Reagents and Conditions:

(i) (a) SOCl$_2$, dry MeOH, 0° C. to rt, 24 h; (b) (Boc)$_2$O, Et$_3$N, THF, 0° C. to rt, 8 h; (ii) (CH$_3$O)$_2$P(O)CH$_3$, nBuLi, THF, −78° C.; (iii) EtOOCCHO, K$_2$CO$_3$, EtOH, 25° C.; (iv) H$_2$, Pd/C, EtOAc, rt; (v) 0.5N LiOH, THF-MeOH (8:2 ratio), rt; (vi) (a) L-proline benzyl ester hydrochloride, EDC.HCl, HOBt, iPr$_2$NEt (2.0 equiv), DMF/CH$_2$Cl$_2$, rt, 48 h; (b) H$_2$, Pd/C, EtOAc-MeOH (3:1 ratio), rt, for 11a; (vii) (a) L-tryptophan methyl ester, EDC.HCl, HOBt, iPr$_2$NEt (1.0 equiv), DMF/CH$_2$Cl$_2$, rt; (b) 0.5N LiOH, THF-MeOH (8:2 ratio), rt, for 11b; (viii) (a) L-phenylalanine methyl ester hydrochloride, EDC.HCl, HOBt, iPr$_2$NEt (2.0 equiv), DMF/CH$_2$Cl$_2$, rt; (b) 0.5N LiOH, THF-MeOH (8:2 ratio), rt, for 11c; and (ix) (a) 0.5M TFA, CH$_2$Cl$_2$, 0° C. to rt, 2 h; (b) benzoyl chloride, pyridine, rt, 24 h; (c) H$_2$, Pd/C, EtOAc-MeOH (3:1 ratio), rt, 48 h.

It will be apparent to a person skilled in the art that many compounds other than the above analogs of keto-ACE (i.e. compounds 5b, 5c and 11a) could be produced according to the process described herein, mainly by inserting novel substituents (functionalities) in the P2, P1, P1′, and P2′ positions. For example, keto-ACE is essentially Bnz-Phe-Gly-Pro; 11a is tert-butyl-Phe-Gly-Pro; 5b is Bnz-Phe-Gly-Trp; and 5c is Bnz-Phe-Gly-Phe. Numerous variations on this theme can be devised, with both natural and non-natural amino acid side-chain substituents. For example, new ACE derivatives which are symmetric and asymmetric ketomethylene peptidomimetics, preferably a heptapeptide, with P2, P1, P1′ and P2′ groups where P2 is amino-benzoly, P1 is Phe, P1′ is Ala, Trp, Arg or Lys, ethyl or butyl or tertiary-butyl, and P2′ is Trp or Phe, or analogues thereof. It will also be possible to alter the keto function (which is the Zn-binding function) to other Zn-binding groups, such as carboxylate, hydroxamates, boronates, phosphonates, phosphoramides, guanidinium, sulfates, vanidates, silanols, and silanediols. It is also envisaged that the P2 group (the Bnz group in all of these compounds) may not be required, thus making it possible for compounds to be smaller by the equivalent of one amino acid.

The invention will now be described in more detail with reference to the following non-limiting examples.

EXAMPLES

General Procedure

All reactions were carried out under a nitrogen atmosphere, unless otherwise specified. Reactions were monitored by TLC using Merck 60 F$_{254}$ precoated silica gel plates. Detection was effected by observation under a UV lamp (wavelength of 254 nm) and developed with I$_2$. Column chromatography was carried out on silica gel and the eluent mixture used is specified in each experiment. Anhydrous solvents like dichloromethane were distilled from phosphorous pentoxide and stored over molecular sieves type 4 Å. All other anhydrous solvents were obtained from Aldrich or Sigma or Merck Chemical Co. All melting points were determined using a Kofler hot plate apparatus and are uncorrected. Specific rotations ($[\alpha]_D$) were measured at 20° C., unless otherwise specified, using a Perkin-Elmer 141 polarimeter and are recorded in units of $10^{-1}$° cm$^2$ g$^{-1}$. NMR spectra were obtained on a Varian Mercury 300 MHz or Varian Unity 400 MHz spectrometer. Chemical shifts are reported in ppm relative to the residual signal of the solvent used. The coupling constants, where specified, are given in hertz (Hz). Mass spectroscopy was carried out on a VG70SEQ instrument using the field regulation electron impact ionization in the positive mode, and 3000 resolutions in the high mode at 8 Kvolts and a scan rate of 4 sec/decade.

Example 1

Synthesis of N-Benzoyl-L-phenylalanine Methyl Ester (1)

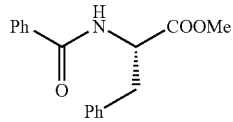

Thionyl chloride (1.63 mL, 22.30 mmol, 2.4 eq) was added dropwise to a solution of N-benzoyl protected-L-phenylalanine (2.50 g, 9.30 mmol, 1.0 eq) in dry MeOH (30 mL) at 0° C. The reaction mixture was allowed to warm to room temperature and the solution was stirred for a further 24 h, then concentrated under vacuum. Purification of the crude by column chromatography on silica gel elution with 25% EtOAc-hexane afforded N-benzoyl-L-phenylalanine methyl ester 1 as a pale yellow viscous oil in quantitative yield: $R_f$ 0.36 (25% EtOAc-hexane); $^1$H NMR (300 MHz, CDCl$_3$) $\delta_H$ 3.22 (2H, m, —CH$_2$Ph), 3.73 (3H, s, —OMe), 5.06 (1H, dd, J=6.0, and 11.7 Hz, —CH—), 6.74 (1H, d, J=7.5 Hz, —NH—) and 7.10-7.78 (10H, m, Ar—H).

Example 2

Synthesis of Dimethyl [(3S)-3-[(N-benzoyl)amino-]-2-oxo-4-phenyl-butyl]-phosphonate (2)

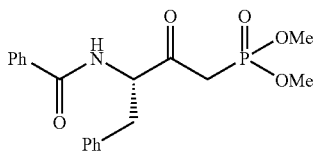

A solution of dimethyl methylphosphonate (3.06 mL, 28.27 mmol, 8.0 eq) in anhydrous THF (30 mL) was cooled to −78° C. and 2.5 N n-BuLi (2.66 mL, 28.60 mmol, 8.0 eq) was added dropwise. After addition, the solution was stirred at −78° C. for 30 min and then a solution of compound 1 (1.00 g, 3.53 mmol, 1.0 eq) in anhydrous THF (20 mL) was added slowly. The resulting mixture was stirred at −78° C. for 1 h and then at ambient temperature for 1 h. The solution was acidified with 10% AcOH (20 mL), extracted with EtOAc (3×50 mL). The extract was washed with 10% NaHCO$_3$, brine, dried over anhydrous MgSO$_4$ and evaporation of the solvent gave a crude residue, which was subjected to column chromatography on silica gel elution with 100% EtOAc afforded dimethyl [(3S)-3-[(N-benzoyl)amino]-2-oxo-4-phenyl-butyl]phosphonate 2 as a pale yellow oil (0.876 g, 66%): $R_f$ 0.34 (EtOAc); $^1$H NMR (300 MHz, CDCl$_3$) $\delta_H$ 3.10 (2H, m, —CH$_2$Ph), 3.34 (2H, m, —CH$_2$—), 3.69 and 3.73 (6H, 2xs, 2xOMe), 5.10 (1H, m, —CH—) and 7.18-7.82 (10H, m, Ar—H).

Example 3

Synthesis of Ethyl Glyoxylate $$EtOOC\diagdown^{CHO}$$

A solution of diethyl-L-tartrate (2.02 g, 9.80 mmol, 1.0 eq) in anhydrous Et$_2$O (15 mL) under N$_2$ was cooled in an ice-water bath and the paraperiodic acid (H$_5$IO$_6$) (2.24 g, 9.80 mmol, 1.0 eq) was added in portion over 1 h. The resulting milky reaction mixture was then stirred for a further 2 h, until the ether become almost clear and a white solid separated. The ether phase was decanted, dried with 4 Å molecular sieves. Evaporation of the solvent gave the crude ethyl glyoxylate in ca. 80%, which was used directly in the next step without further purifications.

Example 4

Synthesis of Ethyl (E/Z)-(5S)-5-[(N-benzoyl)amino]-4-oxo-6-phenyl-2-hexenoate (3)

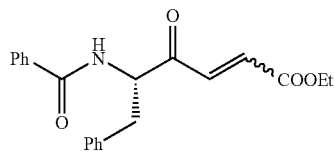

To a stirred solution of the phosphonate 2 (1.50 g, 3.997 mmol, 1.0 eq) and freshly prepared ethyl glyoxylate (0.41 g, 3.997 mmol, 1.0 eq) in absolute EtOH (60 mL) was added anhydrous K$_2$CO$_3$ (0.55 g, 3.997 mmol, 1.0 eq) in small portions for a period of 15 min. The resulting mixture was stirred at room temperature for 2 h, filtered and the solution neutralized with glacial acetic acid. Evaporation of the solvent and then column chromatography on silica gel elution with 50% EtOAc-hexane afforded ethyl (E/Z)-(5S)-5-[(N-benzoyl)amino]-4-oxo-6-phenyl-2-hexenoate 3 as a clear yellow oil mixture (1.13 g, 80%) in a 85:15/trans:cis ratio: $R_f$ 0.40 and 0.42 (50% EtOAc-hexane, for cis and trans respectively); $^1$H NMR (400 MHz, CDCl$_3$) $\delta_H$ 1.31 (3H, t, J=7.2 Hz, CH$_2$CH$_3$), 1.32 (3H, t, J=7.2 Hz, CH$_2$CH$_3$), 3.21-3.32 (4H, m, −2×CH$_2$Ph), 4.12 (2H, q, J=7.1 Hz, —OCH$_2$—), 4.25 (2H, q, J=7.0 Hz, —OCH$_2$—), 5.22 (1H, dd, J=6.2 and 12.0 Hz, —CH—), 5.32 (1H, m, —CH—), 6.07 and 6.47 (2H, 2xd, $J_{cis}$=12.0 Hz, —C=CH), 6.81 and 7.19 (2H, 2xd, $J_{trans}$=16.0 Hz, —C=CH) and 7.11-7.76 (20H, m, Ar—H).

Example 5

Synthesis of Ethyl-(5S)-5-[(N-benzoyl)amino]-4-oxo-6-phenyl-hexanoate (3a)

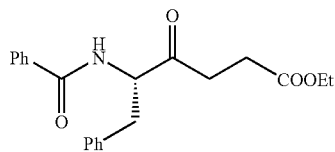

To a stirred solution of compound 3 (1.0 g, 2.846 mmol, 1.0 eq) in dry EtOAc (50 mL) was added 10% Pd/C (0.35 g) and the resulting mixture stirred at room temperature under 1 atmosphere of hydrogen for 2 h. Filtration of the black Pd residue and evaporation of the filtrate gave a crude yellow residue. Column chromatography on silica gel elution with 33% EtOAc-hexane afforded the intermediate compound ethyl-(5S)-5-[(N-benzoyl)amino]-4-oxo-6-phenyl-hexanoate 3a as a white solid (0.794 g, 80%): mp 112-114° C.; $R_f$ 0.30 (40% EtOAc-hexane); IR (KBr) ν 1690 (CO), 1740 (CO), 3300 (CONH) cm$^{-1}$; $^1$H NMR (300 MHz, CDCl$_3$) $\delta_H$ 1.25 (3H, t, J=7.2 Hz, CH$_2$CH$_3$), 2.60 (2H, t, J=6.6 Hz, —CH$_2$CO—), 2.81 (2H, t, J=6.6 Hz, —CH$_2$CO), 3.16 (1H, dd, J=6.9 and 14.3 Hz, —CH$_\alpha$Ph), 3.30 (1H, dd, J=6.9 and 14.4 Hz, —CH$_\beta$Ph), 4.13 (2H, q, J=6.9 and 14.1 Hz, —OCH$_2$—), 5.07 (1H, q, J=6.6 Hz, —CH—), 6.76 (1H, d, J=6.9 Hz, —NH—) and 7.15-7.75 (10H, m, Ar—H); $^{13}$C NMR (75 MHz, CDCl$_3$) $\delta$c 14.1, 27.8, 35.2, 37.2, 59.4, 60.7, 127.0 (2C), 127.1 (2C), 128.6 (2C), 128.7 (2C), 129.3, 131.7, 133.9, 136.1, 166.9, 172.4 and 206.9; HRMS m/z calcd for C$_{21}$H$_{23}$NO$_4$ (M$^+$) 353.16072, found 353.16271. Anal. Calcd. for C$_{21}$H$_{23}$NO$_4$: C, 71.37; H, 6.56; N, 3.96. Found: C, 70.92; H, 6.34; N, 3.89.

Example 6

Synthesis of (5S)-5-[(N-benzoyl)amino-]4-oxo-6-phenyl-hexanoic acid (4)

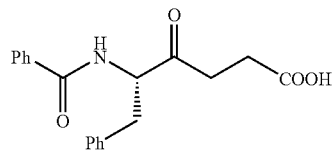

To a stirred solution of ethyl-(5S)-5-[(N-benzoyl)amino]-4-oxo-6-phenyl-hexanoate (0.300 g, 0.8489 mmol, 1.0 eq) in THF-MeOH (8:2 ratio)(10 mL) was added 0.5N LiOH (10 mL) and the resulting mixture was stirred at room temperature for 3 h. The reaction mixture was then neutralized with glacial acetic acid and then extracted with EtOAc (3×25 mL). The organic extract was dried over anhydrous MgSO$_4$ and evaporation of the solvent afforded a crude yellow residue. Column chromatography on silica gel elution with 100% EtOAc afforded (5S)-5-[(N-benzoyl)amino]-4-oxo-6-phenyl-hexanoic acid 4 as a white solid (0.232 g, 82%): mp 143-146° C. (lit.$^{12}$ mp 142-143° C.); $R_f$ 0.25 (EtOAc); IR (KBr) ν 1685 (CO), 1760 (CO), 3150 (COOH) cm$^{-1}$; $^1$H NMR (400 MHz, CDCl$_3$) $\delta_H$ 2.48 (2H, t, J=6.8 Hz, —CH$_2$CO), 2.72 (2H, t, J=7.0 Hz, —CH$_2$CO), 2.97 (1H, dd, J=6.4 and 14.4 Hz, —CH$_\alpha$Ph), 3.18 (1H, dd, J=6.4 and 14.4 Hz, —CH$_\beta$Ph), 3.81 (2H, br s, —NH and —COOH), 4.87 (1H, t, J=6.8 Hz, —CH—) and 7.05-7.65 (10H, m, Ar—H); $^{13}$C NMR (100 MHz, CDCl$_3$) $\delta_C$ 27.5, 34.9, 36.4, 59.5, 126.8, 126.9, 127.9, 128.4 (2C), 128.5 (2C), 129.1 (2C), 131.7, 133.5, 136.3, 167.9, 174.6 and 207.5; HRMS m/z calcd for C$_{19}$H$_{19}$NO$_4$ (M$^+$) 325.12854, found 353.13141.

Example 7

Synthesis of L-phenylalanine methyl ester hydrochloride (NACE 68E)$^{30}$

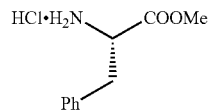

Thionyl chloride (3.10 mL, 42.38 mmol, 1.4 eq) was added dropwise to a suspension of L-phenylalanine (5.0 g, 30.27 mmol, 1.0 eq) in dry MeOH (30 mL) at 0° C. The cold bath was removed and the solution was stirred at room temperature for 24 h, then concentrated under vacuum. The residue was triturated with cold Et$_2$O, filtered and wash with cold Et$_2$O and the filtrate evaporated in vacuo to give the L-phenylalanine methyl ester hydrochloride as a white crystalline solid in quantitative yield; IR (KBr) ν 1740 (CO), 3305 (NH) cm$^{-1}$; $^1$H NMR (300 MHz, CDCl$_3$) $\delta_H$ 1.46 (2H, s, —NH$_2$), 2.75 (1H, dd, J=6.8 and 14.1 Hz, —CH$_\alpha$Ph), 3.00 (1H, dd, J=6.7 and 14.2 Hz, —CH$_\beta$Ph), 3.72 (3H, s, OMe), 4.65 (1H, t, J=6.8 Hz, —CH—) and 7.10-7.30 (5H, m, Ar—H), which was sufficiently pure and used directly in the next step.

Example 8

Synthesis of L-tryptophan methyl ester (NACE 51)$^{31}$

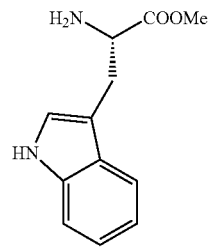

Thionyl chloride (4.25 mL, 58.10 mmol, 2.4 eq) was added dropwise to a suspension of L-tryptophan (5.0 g, 24.48 mmol, 1.0 eq) in dry MeOH (50 mL) at −15° C. The cold bath was removed and the solution was stirred at room temperature for 24 h, then concentrated under vacuum at 40° C. gave a residue which was dissolved in H$_2$O (75 mL) and then neutralized with Na$_2$CO$_3$ to a pH 8. Extraction with CHCl$_3$ (3×50 mL) and dried over anhydrous MgSO$_4$. Evaporation of the solvent gave the L-tryptophan methyl ester as a brick-red viscous oil (5.37 g, 98%); IR (liquid film) ν 1755 (CO), 3290 (NH) cm$^{-1}$; $^1$H NMR (300 MHz, CDCl$_3$) $\delta_H$ 1.78 (2H, s, —NH$_2$), 3.10 (1H, dd, J=6.8 and 14.8 Hz, —CH$_\alpha$Trp), 3.32 (1H, dd, J=6.0 and 14.8 Hz, —CH$_\beta$Trp), 3.80 (3H, s, OMe), 4.50 (1H, t, J=6.8 Hz, —CH—), 7.06 (1H, t, J=7.4 Hz, H-5'), 7.13 (1H, t, J=7.4 Hz, H-6'), 7.23 (1H, s, H-2'), 7.39 (1H, d, J=7.8 Hz, H-7'), 7.55 (1H, d, J=7.8 Hz, H-4') and 8.47 (1H, s, pyrrol NH), which was sufficiently pure and used directly in the next step.

Example 9

Synthesis of (5S)-5-[(N-benzoyl)amino-]4-oxo-6-phenyl-hexanoyl-L-proline benzyl ester (NACE 81)

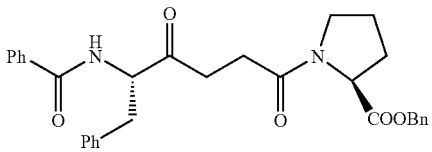

A solution of the free acid compound 4 (100 mg, 0.3055 mmol, 1.0 eq.) and L-proline benzyl ester hydrochloride (74 mg, 0.3055 mmol, 1.0 eq.) in dry CH$_2$Cl$_2$ (10 mL) was cooled at 0° C. 1-Hydroxybenzotriazole hydrate (HOBt) (42 mg, 0.3055 mmol, 1.0 eq.), N-ethyl-N'-(dimethylaminopropyl)-carbodiimide hydrochloride (EDC.HCl) (59 mg, 0.3055 mmol, 1.0 eq.) and iPr$_2$NEt (0.10 mL, 0.6110 mmol, 2.0 eq.) were added and the resulting mixture stirred at 0° C. for 2 h. The cooling bath was removed and the reaction mixture then stirred for a further 48 h at room temperature. The reaction mixture was diluted with H$_2$O (30 mL) and the extracted with EtOAc (3×30 mL). The combined organic extract were washed sequentially with saturated aqueous NaHCO$_3$ (30 mL), brine (30 mL), and dried over anhydrous MgSO$_4$. Evaporation of the solvent gave a crude residue, which was subjected to column chromatography on silica gel elution with 50% EtOAc-hexane afforded the desired compound (5S)-5-[(N-benzoyl)amino]-4-oxo-6-phenyl-hexanoyl-L-proline benzyl ester as a pale yellow viscous oil which foams (0.138 g, 88%); R$_f$ 0.23 (50% EtOAc-hexane); IR (liquid film) v 1726 (CO), 3200 (NH) cm$^{-1}$; $^1$H NMR (300 MHz, CDCl$_3$) δ$_H$ 1.98 (2H, m, —CH$_2$), 2.21 (2H, m, —CH$_2$), 2.65 (2H, m, —CH$_2$CO), 3.00 (1H, m, —CH$_\alpha$Ph), 3.12 (1H, m, —CH$_\beta$Ph), 3.35 (2H, m, —CH$_2$CO), 3.60 (2H, m, —CH$_2$N), 4.52 (1H, m, —CHN), 5.03 (1H, m, —CH—), 5.14 (2H, dd, J=1.8 and 8.4 Hz, —OCH$_2$Ph), 6.93 (1H, d, J=6.9 Hz, —NH—) and 7.15-7.77 (15H, m, Ar—H); $^{13}$C NMR (75 MHz, CDCl$_3$) δC 22.8, 24.7, 28.3, 28.9, 29.2, 34.1, 34.6, 36.8, 46.5, 46.9, 58.9, 59.6, 66.7, 66.8, 126.8, 126.9, 127.0, 127.9, 128.3, 128.5, 128.7 (2C), 129.4, 131.6, 133.9, 135.7, 136.7, 166.9, 170.3, 171.9 and 207.4; HRMS m/z calcd for C$_{31}$H$_{32}$N$_2$O$_5$ (M$^+$) 512.23436, found 512.23112.

Example 10

Synthesis of (5S)-5-[(N-benzoyl)amino]-4-oxo-6-phenyl-hexanoyl-L-tryptophan methyl ester (NACE 82)

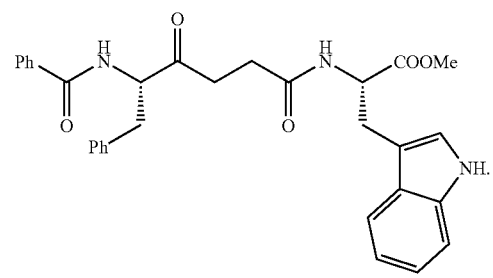

The experimental procedure employed for the synthesis of (5S)-5-[(N-benzoyl)amino]-4-oxo-6-phenyl-hexanoyl-L-proline benzyl ester was followed using the free acid compound 4 (200 mg, 0.6109 mmol, 1.0 eq.), L-tryptophan methyl ester (133 mg, 0.6109 mmol, 1.0 eq.), 1-Hydroxybenzotriazole hydrate (HOBt) (83 mg, 0.6109 mmol, 1.0 eq.), N-ethyl-N'-(dimethylaminopropyl)-carbodiimide hydrochloride (EDC.HCl) (117 mg, 0.6109 mmol, 1.0 eq.), iPr$_2$NEt (0.11 mL, 0.6110 mmol, 1.0 eq.) and dry DMF/CH$_2$Cl$_2$ (2:8 ratio)(10 mL). Work-up as usual and column chromatography on silica gel elution with 100% EtOAc afforded the (5S)-5-[(N-benzoyl)amino]-4-oxo-6-phenyl-hexanoyl-L-tryptophan methyl ester as a yellow solid (0.290 g, 90%); mp 88-90° C.; R$_f$ 0.50 (EtOAc); IR (KBr) v 1760 (CO), 3230 (NH) cm$^{-1}$; $^1$H NMR (300 MHz, CDCl$_3$) δ$_H$ 2.44 (2H, m, —CH$_2$CO), 2.82 (2H, m, —CH$_2$CO), 3.06 (1H, m, —CH$_\alpha$Ph), 3.28 (3H, m, —CH$_\beta$Ph and —CH$_2$Trp), 3.67 (3H, s, —OMe), 4.90 (1H, m, —CH—), 4.99 (1H, m, —CH—), 6.17 (1H, dd, J=2.7 and 7.5 Hz, —NH), 6.88 (1H, d, J=6.9 Hz, —NH), 7.00 (1H, dd, J=2.8 and 6.4 Hz, Trp-H-5'), 7.02-7.56 (12H, m, Ar—H), 7.68 (1H, d, J=1.8 Hz, Trp-H-2'), 7.71 (1H, d, J=1.8 Hz, Ar—H) and 8.27 (1H, br-s, —NH); $^{13}$C NMR (75 MHz, CDCl$_3$) δ$_C$ 27.6, 29.7, 35.0, 35.1, 36.8, 36.9, 52.3, 53.0, 59.4, 59.6, 109.9, 111.3, 118.5, 119.7, 122.2, 123.0, 127.0, 127.6 (2C), 128.5, 128.6 (2C), 129.3, 131.8, 133.8, 136.1, 136.2, 167.1, 171.1, 172.3 and 207.5; HRMS m/z calcd for C$_{31}$H$_{31}$N$_3$O$_5$ (M$^+$) 525.22637, found 525.22637.

Example 11

Synthesis of (5S)-5-[(N-benzoyl)amino]-4-oxo-6-phenyl-hexanoyl-L-phenylalanine methyl ester (NACE 83)

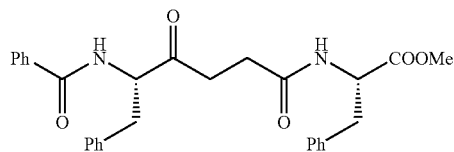

The experimental procedure employed for the synthesis of (5S)-5-[(N-benzoyl)amino]-4-oxo-6-phenyl-hexanoyl-L-proline benzyl ester was followed using the free acid compound 4 (200 mg, 0.6109 mmol, 1.0 eq.), L-phenylalanine methyl ester (110 mg, 0.6109 mmol, 1.0 eq.), 1-Hydroxybenzotriazole hydrate (HOBt) (83 mg, 0.6109 mmol, 1.0 eq.), N-ethyl-AF-(dimethylaminopropyl)-carbodiimide hydrochloride (EDC.HCl) (117 mg, 0.6109 mmol, 1.0 eq.), iPr₂NEt (0.11 mL, 0.6110 mmol, 1.0 eq.) and dry DMF/CH₂Cl₂ (2:8 ratio)(10 mL). Work-up as usual and column chromatography on silica gel elution with 66% EtOAc-hexane afforded the (5S)-5-[(N-benzoyl)amino]-4-oxo-6-phenyl-hexanoyl-L-phenylalanine methyl ester as a cream white solid (0.274 g, 92%); mp 106-109° C.; $R_f$ 0.45 (66% EtOAc-hexane); IR (KBr) v 1750 (CO), 3290 (NH) cm⁻¹; ¹H NMR (300 MHz, CDCl₃) $\delta_H$ 2.50 (2H, m, —CH₂CO), 2.85 (2H, m, —CH₂CO), 3.11 (3H, m, —CH$_\alpha$Ph and —CH₂Ph), 3.30 (1H, dd, J=6.6 and 14.4 Hz, —CH$_\beta$Ph), 3.71 (3H, s, —OMe), 4.84 (1H, m, —CH—), 5.02 (1H, ddd, J=2.4, 6.9 and 9.0 Hz, —CH—), 6.03 (1H, d, J=7.2 Hz, —NH), 6.84 (1H, d, J=6.0 Hz, —NH) and 7.06-7.74 (15H, m, Ar—H); ¹³C NMR (75 MHz, CDCl₃) $\delta_C$ 29.6, 29.7, 35.1, 35.2, 37.0, 37.9, 52.3, 53.2, 59.4, 59.5, 127.0 (2C), 127.1, 127.2, 128.6 (2C), 128.7 (2C), 129.3, 129.4 (2C), 131.7, 133.9, 135.8, 136.2, 167.0, 171.0, 171.9 and 207.4; HRMS m/z calcd for C₂₉H₃₀N₂O₅ (M⁺) 486.21829, found 486.21547. Anal. Calcd. for C₂₉H₃₀N₂O₅: C, 71.59; H, 6.21; N, 5.96. Found: C, 71.43; H, 6.23; N, 5.76.

Example 12

Synthesis of (5S)-5-[(N-benzoyl)amino]4-oxo-6-phenyl-hexanoyl-L-proline (5a)<sup>±</sup>

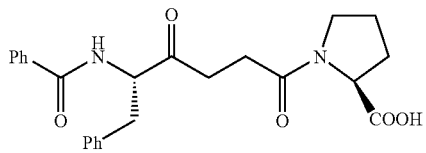

To a stirred solution of the (5S)-5-[(N-benzoyl)amino]-4-oxo-6-phenyl-hexanoyl-L-proline benzyl ester (100 mg, 0.1951 mmol) in dry EtOAc-MeOH (3:1 ratio) (10 mL) was added 10% Pd/C (100 mg) and the resulting mixture stirred at room temperature under 1 atmosphere of hydrogen for 24 h. Filtration of the black Pd residue and evaporation of the filtrate gave a pale yellow crude residue. Column chromatography on silica gel elution with 37% MeOH-EtOAc afforded the (5S)-5-[(N-benzoyl)amino]-4-oxo-6-phenyl-hexanoyl-L-proline 5a as a white solid powder (68 mg, 82%): mp 148-149° C. (lit.¹² mp 151-153° C.); $R_f$ 0.28 (37% MeOH-EtOAc); IR (KBr) v 1765 (CO), 3300 (broad, COOH) cm⁻¹; ¹H NMR (300 MHz, CD₃OD) $\delta_H$ 2.01 (2H, m, —CH₂), 2.51 (4H, m, —CH₂CO and —CH₂CH₂N), 2.78 (2H, m, —CH₂CO), 3.02-3.38 (4H, m —CH₂Ph and —CH₂N—), 4.84 (1H, m, —CH—), 4.98 (1H, m, —CH—) and 7.08-7.68 (10H, m, Ar—H); ¹³C NMR (75 MHz, CD₃OD) $\delta_C$ 22.6, 24.5, 28.6, 34.3, 36.2, 46.4, 59.9, 61.8, 126.6 (2C), 126.8 (2C), 128.4, 128.9 (2C), 129.0, 131.6, 133.5, 136.6, 136.9, 167.9, 171.0, 179.3 and 208.9; HRMS m/z calcd for C₂₄H₂₆N₂O₅ (M⁺) 422.18417, found 422.18417. [<sup>±</sup> The carboxylic acid and amide protons were not observed, presumably, due to rapid exchange with water in the deuteriated NMR solvent.]

Example 13

Synthesis of (5S)-5-[(N-benzoyl)amino]-4-oxo-6-phenyl-hexanoyl-L-tryptophan (5b)<sup>±</sup>

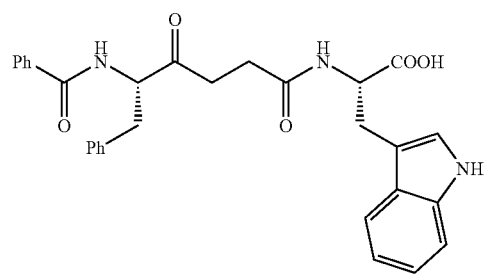

To a stirred solution of the compound (5S)-5-[(N-benzoyl)amino]-4-oxo-6-phenyl-hexanoyl-L-tryptophan methyl ester (170 mg, 0.3222 mmol, 1.0 eq.) in a mixture THF-MeOH (ratio 3:2) (10 mL) was added 0.5N LiOH (5.0 mL). The resulting yellowish mixture was stirred at room temperature for 30 min during which TLC shows the complete disappearance of the starting material. The reaction mixture was then neutralized with glacial acetic acid and the extracted with EtOAc (3×25 mL), dried over anhydrous MgSO₄ and evaporation of the solvent gave a crude residue, which was subjected to column chromatography on silica gel elution with 30% MeOH-EtOAc afforded the free acid (5S)-5-[(N-benzoyl)amino]-4-oxo-6-phenyl-hexanoyl-L-tryptophan 5b as a pale yellow solid (0.158 g, 95%); mp 171-173° C.; $R_f$ 0.38 (30% MeOH-EtOAc); IR (KBr) v 1720 (CO), 3250 (broad, COOH) cm⁻¹; ¹H NMR (400 MHz, CDCl₃) $\delta_H$ 2.31 (2H, m, —CH₂CO), 2.70 (2H, m, —CH₂CO), 2.96 (1H, m, —CH$_\alpha$Ph), 3.24 (3H, m, —CH$_\beta$Ph and —CH₂Trp),), 4.84 (1H, m, —CH—), 4.90 (1H, m, —CH—), 6.49 (1H, t, J=7.2 Hz, —NH), 6.92-7.66 (16H, m, Ar—H and —NH) and 8.48 (1H, d, J=6.0 Hz, —NH); ¹³C NMR (100 MHz, CDCl₃) $\delta_C$ 27.2, 29.5, 35.0, 35.1, 36.5, 53.2, 59.5, 59.6, 109.5, 111.4, 118.5, 119.6, 122.0, 123.5, 127.0, 127.1 (2C), 127.4, 128.6, 128.7 (2C), 129.2, 132.0, 133.5, 136.1, 167.7, 172.4, 174.6 and 207.8; HRMS m/z calcd for C₃₀H₂₉N₃O₅ (M⁺) 511.21072, found 511.21072. [<sup>±</sup> The carboxylic acid and amide protons were not observed, presumably, due to rapid exchange with water in the deuteriated NMR solvent.]

Example 14

Synthesis of (5S)-5-[(N-benzoyl)amino]-4-oxo-6-phenyl-hexanoyl-L-phenylalanine (5c)<sup>±</sup>

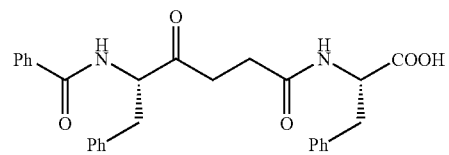

The experimental procedure employed for the synthesis of compound 5b was followed using the (5S)-5-[(N-benzoyl) amino]-4-oxo-6-phenyl-hexanoyl-L-phenylalanine methyl ester (200 mg, 0.4094 mmol, 1.0 eq.), 0.5N LiOH (5.0 mL) and a mixture THF-MeOH (ratio 3:2) (10 mL) was added 0.5N LiOH (5.0 mL). Work-up and column chromatography on silica gel elution with 20% MeOH-EtOAc afforded the free acid (5S)-5-[(N-benzoyl)amino]-4-oxo-6-phenyl-hexanoyl-L-phenylalanine 5c as a yellow oil (0.187 g, 97%); IR (liquid film) v 1720 (CO), 3100 (broad, COOH) cm$^{-1}$; $^1$H NMR (300 MHz, CDCl$_3$) $\delta_H$ 2.46 (2H, m, —CH$_2$CO), 2.80 (2H, m, —CH$_2$CO), 3.00-3.31 (4H, m, 2×—CH$_2$Ph), 4.81 (1H, q, J=6.0 Hz), 4.98 (1H, ddd, J=2.5, 7.0 and 9.0 Hz, —CH—), 6.30 (1H, m, —NH), 6.94 (1H, t, J=9.3 Hz, Ar—H) and 7.10-7.74 (16H, m, Ar—H and —NH); $^{13}$C NMR (75 MHz, CDCl$_3$) $\delta_C$ 29.1, 29.7, 35.3, 36.8, 37.3, 53.3, 59.5, 59.6, 67.7, 127.1 (2C), 127.2 (2C), 128.5, 128.6, 128.7, 129.2, 129.3, 129.4, 131.9, 133.5, 135.8, 136.1, 167.5, 172.0, 174.9 and 207.7; HRMS m/z calcd for C$_{28}$H$_{28}$N$_2$O$_5$ (M$^+$) 472.19982, found 472.19982. [± The carboxylic acid and amide protons were not observed, presumably, due to rapid exchange with water in the deuteriated NMR solvent.]

Example 15

Synthesis of N-Boc-L-phenylalanine methyl ester (6)

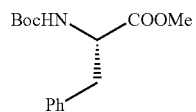

Thionyl chloride (3.10 mL, 42.38 mmol, 1.4 eq) was added dropwise to a suspension of L-phenylalanine (5.0 g, 30.27 mmol, 1.0 eq) in dry MeOH (30 mL) at 0° C. The cold bath was, removed and the solution was stirred at room temperature for 24 h, then concentrated under vacuum. The residue was triturated with cold Et$_2$O, filtered and wash with cold Et$_2$O and the filtrate evaporated in vacuo to give the methyl ester hydrochloride as a white crystalline solid. To a suspension of the methyl ester hydrochloride in THF (30 mL) at 0° C. was added Et$_3$N (5.50 mL, 39.45 mmol, 1.2 eq) and then followed by a solution of (Boc)$_2$O (8.61 g, 39.45 mmol, 1.2 eq) in THF (30 mL). The resulting mixture was stirred at room temperature for 8 h. The solvent was reduced to half its original volume, addition of H$_2$O (20 mL) and then extracted with EtOAc (3×30 mL). The organic extract was dried over anhydrous MgSO$_4$ and evaporation of the solvent afforded the N-Boc-L-phenylalanine methyl ester 6 as a pale yellow oil in quantitative yield; R$_f$ 0.41 (20% EtOAc-hexane); $^1$H NMR (300 MHz, CDCl$_3$) $\delta_H$ 1.39 (9H, s, (CH$_3$)$_3$), 3.05 (2H, m, —CH$_2$—), 3.64 (3H, s, OMe), 4.53 (1H, q, J.=7.8 Hz, —CH—), 5.06 (1H, d, J=9.0 Hz, —NH—) and 7.06-7.26 (5H, m, Ar—H), which was used directly in the next step without further purification.

Example 16

Synthesis of dimethyl [(3S)-4-phenyl-3-[(tert-butyloxycarbonyl)amino]-2-oxobutyl]phosphonate (7)

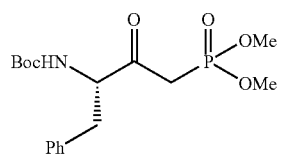

A solution of dimethyl methylphosphonate (3.10 mL, 28.60 mmol, 8.0 eq) in anhydrous THF (30 mL) was cooled to −78° C. and 2.5 N n-BuLi (2.70 mL, 28.60 mmol, 8.0 eq) was added dropwise. After addition, the solution was stirred at −78° C. for 30 min and then a solution of compound 6 (1.00 g, 3.58 mmol, 1.0 eq) in anhydrous THF (20 mL) was added slowly. The resulting mixture was stirred at −78° C. for 1 h and then at ambient temperature for 1 h. The solution was acidified with 10% AcOH (20 mL), extracted with EtOAc (3×50 mL). The extract was washed with 10% NaHCO$_3$, brine, dried over anhydrous MgSO$_4$ and evaporation of the solvent gave a crude residue, which was subjected to column chromatography on silica gel elution with 100% EtOAc afforded the compound dimethyl [(3S)-4-phenyl-3-[(tert-butyloxycarbonyl)amino]-2-oxobutyl]-phosphonate 7 as a clear oil (0.797 g, 59%), which crystallizes in hexane as a white solid; mp 78-81° C. (lit.[1] mp 76-78° C.); R$_f$ 0.38 (EtOAc); $^1$H NMR (300 MHz, CDCl$_3$) $\delta_H$ 1.38 (9H, s, (CH$_3$)$_3$), 2.84-3.32 (4H, m), 3.74 and 3.78 (6H, 2xs, 2xOMe), 4.55 (1H, q, J=8.4 Hz, —CH—), 5.28 (1H, d, J=8.4 Hz, —NH—), and 7.16-7.32 (5H, m, Ar—H).

Example 17

Synthesis of ethyl-(E/Z)-(5S)-6-phenyl-5-[(tert-butyloxycarbonyl)amino]-4-oxo-2-hexenoate (8)

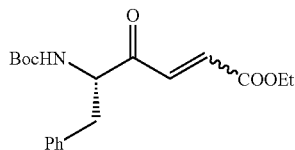

To a stirred solution of the phosphonate 7 (0.50 g, 1.347 mmol, 1.0 eq) and freshly prepared ethyl glyoxylate (0.14 g, 1.347 mmol, 1.0 eq) in absolute EtOH (15 mL) was added anhydrous K$_2$CO$_3$ (0.19 g, 1.347 mmol, 1.0 eq) in small portions for a period of 15 min. The resulting mixture was stirred at room temperature for 2 h, filtered and the solution neutralized with glacial acetic acid. Evaporation of the solvent and then column chromatography on silica gel elution with 20% EtOAc-hexane gave the ethyl-(E/Z)-(5S)-6-phenyl-5-[(tert-butyloxycarbonyl)amino]4-oxo-2-hexenoate 8 as a yellow solid mixture (0.407 g, 87%) in a 80:20/trans:cis ratio: R$_f$ 0.52 and 0.54 (20% EtOAc-hexane, for cis and trans respectively); $^1$H NMR (300 MHz, CDCl$_3$) $\delta_H$ 1.27 (3H, t, J=7.1 Hz, CH$_2$CH$_3$), 1.31 (3H, t, J=6.9 Hz, CH$_2$CH$_3$), 1.38 (9H, s, (CH$_3$)$_3$), 1.40 (9H, s, (CH$_3$)$_3$), 3.10 (4H, m, 2×—CH$_2$Ph), 4.24 (2H, q, J=6.9, —OCH$_2$—), 4.26 (2H, q, J=7.0, —OCH$_2$—), 4.25 (1H, m, —CH—), 4.65 (1H, m, —CH—), 4.77 (1H, m, —CH—), 5.14 (1H, d, J=7.5 Hz, —NH—), 6.04 and 6.42 (2H, 2xd, J$_{cis}$=12.0 Hz, —C=CH), 6.74 and 7.26 (2H, 2xd, J$_{trans}$=15.6 Hz, —C=CH) and 7.08-7.30 (10H, m, Ar—H).

Example 18

Synthesis of ethyl-(5S)-6-phenyl-5-[(tert-butyloxycarbonyl)amino]-4-oxo-hexanoate (8a)

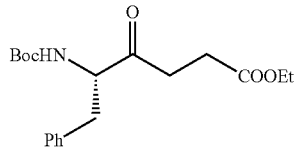

To a stirred solution of compound 8 (0.60 g, 0.864 mmol) in dry EtOAc (30 mL) was added 10% Pd/C (0.20 g) and the resulting mixture stirred at room temperature under 1 atmosphere of hydrogen for 2 h. Filtration of the black Pd residue and evaporation of the filtrate gave a crude yellow residue. Column chromatography on silica gel elution with 25% EtOAc-hexane afforded the intermediate ester compound ethyl-(5S)-6-phenyl-5-[(tert-butyloxycarbonyl)-amino]-4-oxo-hexanoate 8a as a light yellow solid (0.554 g, 92%): mp 56-58° C.; R$_f$ 0.31 (25% EtOAc-hexane); IR (KBr) ν 1650 (CO), 1735 (CO), 3270 (CONH) cm$^{-1}$; $^1$H NMR (400 MHz, CDCl$_3$) δ$_H$ 1.32 (3H, s, J=7.2 Hz, CH$_2$CH$_3$), 1.38 (9H, s, (CH$_3$)$_3$), 2.54 (2H, t, J=6.4 Hz, —CH$_2$CO), 2.74 (2H, m, —CH$_2$CO—), 3.10 (2H, m, —CH$_2$Ph), 4.31 (2H, q, J=7.2 Hz, —OCH$_2$—), 4.53 (1H, m, —CH—), 5.09 (1H, d, J=8.0 Hz, —NH—) and 7.15-7.30 (5H, m, Ar—H); HRMS m/z calcd for C$_{19}$H$_{27}$NO$_5$ (M$^+$) 349.19071, found 349.18892. Anal. Calcd. for C$_{19}$H$_{27}$NO$_5$: C, 65.31; H, 7.79; N, 4.01. Found: C, 65.23; H, 7.79; N, 3.97.

Example 19

Synthesis of (5S)-6-phenyl-5-[(tert-butyloxycarbonyl)-amino]-4-oxo-hexanoic acid (9)

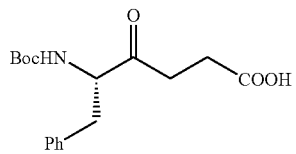

To a stirred solution of the intermediate ethyl-(5S)-6-phenyl-5-[(tert-butyloxy-carbonyl)-amino]4-oxo-hexanoate (0.250 g, 0.716 mmol) in THF-MeOH (8:2 ratio)(10 mL) was added 0.5N LiOH (10 mL) and the resulting mixture was stirred at room temperature for 3 h. The reaction mixture was then neutralized with glacial acetic acid and then extracted with EtOAc (3×25 mL). The organic extract was dried over anhydrous MgSO$_4$ and evaporation of the solvent afforded a crude yellow residue. Column chromatography on silica gel elution with 50% EtOAc-hexane afforded (5S)-6-phenyl-5-[(tert-butyloxycarbonyl)-amino]-4-oxo-hexanoic acid 9 as a cream yellow solid (0.225 g, 98%); mp 108-110° C.; R$_f$ 0.41 (50% EtOAc-hexane); IR (KBr) ν 1730 (CO), 3200 (broad, COOH) cm$^{-1}$; $^1$H NMR (300 MHz, CDCl$_3$) δ$_H$ 1.39 (9H, s, (CH$_3$)$_3$), 2.62-2.73 (4H, m, —COCH$_2$CH$_2$CO), 2.94 (1H, dd, J=6.9 and 13.8 Hz, —CH$_\alpha$Ph), 3.10 (1H, dd, J=6.0 and 13.8 Hz, —CH$_\beta$Ph), 4.54 (1H, m, —CH—), 5.08 (1H, d, J=8.1 Hz, —NH—) and 7.13-7.35 (5H, m, Ar—H); $^{13}$C NMR (75 MHz, CDCl$_3$) δ$_C$ 27.5, 28.3, 35.0, 37.5, 60.1, 80.1, 127.0 (2C), 128.7 (2C), 129.2 (2C), 129.3, 136.2, 155.4, 177.4 and 207.4; HRMS m/z calcd for C$_{17}$H$_{23}$NO$_5$ (M$^+$) 321.15831, found 321.15762. Anal. Calcd. for C$_{17}$H$_{23}$NO$_5$: C, 63.54; H, 7.21; N, 4.36. Found: C, 63.55; H, 7.34; N, 4.30.

Example 20

Synthesis of (5S)-6-phenyl-5-[tert-butyloxycarbonyl)-amino]-4-oxo-hexanoyl-L-proline benzyl ester (10)

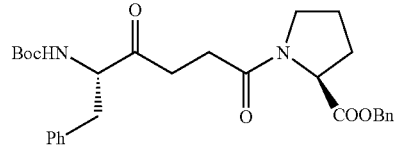

A solution of the free acid compound 9 (200 mg, 0.6224 mmol, 1.0 eq.) and L-proline benzyl ester hydrochloride (150 mg, 0.6224 mmol, 1.0 eq.) in dry CH$_2$Cl$_2$ (15 mL) was cooled at 0° C. 1-Hydroxybenzotriazole hydrate (HOBt) (84 mg, 0.6224 mmol, 1.0 eq.), N-ethyl-N'-(dimethylaminopropyl)-carbodiimide hydrochloride (EDC.HCl) (120 mg, 0.6224 mmol, 1.0 eq.) and iPr$_2$NEt (0.22 mL, 1.245 mmol, 2.0 eq.) were added and the resulting mixture stirred at 0° C. for 2 h. The cooling bath was removed and the reaction mixture then stirred for a further 72 h at room temperature. The reaction mixture was diluted with H$_2$O (30 mL) and the extracted with EtOAc (3×30 mL). The combined organic extract were washed sequentially with saturated aqueous NaHCO$_3$ (30 mL), brine (30 mL), and dried over anhydrous MgSO$_4$. Evaporation of the solvent gave a crude residue, which was subjected to column chromatography on silica gel elution with 33% EtOAc-hexane to afforded the (5S)-6-phenyl-5-[(tert-butyloxycarbonyl)-amino]-4-oxo-hexanoyl-L-proline benzyl ester 10 as a yellow viscous oil (0.255 g, 81%); R$_f$ 0.30 (33% EtOAc-hexane); IR (liquid film) ν 1750 (CO), 3150 (CONH) cm$^{-1}$; $^1$H NMR (300 MHz, CDCl$_3$) δ$_H$ 1.39 (9H, s, (CH$_3$)$_3$), 2.00-2.18 (4H, m, —CH$_2$CH$_2$—), 2.48-2.80 (3H, m, —CH$_2$CO and —CH$_\alpha$Ph), 2.94 (2H, m, —CH$_2$CO), 3.18 (1H, m, —CH$_\beta$Ph), 3.60 (2H, m, —CH$_2$N—), 4.53 (2H, m, 2×—CH—), 5.09 (1H, m, —NH—), 5.15 (2H, dd, J=2.0 and 10.5 Hz, —OCH$_2$Ph) and 7.13-7.38 (10H, m, Ar—H); $^{13}$C NMR (75 MHz, CDCl$_3$) δ$_C$ 21.0, 22.6, 24.7, 28.3, 29.2, 31.4, 31.7, 34.7, 46.5, 59.5, 60.3, 66.7, 126.8 (2C), 127.0, 127.6, 128.1, 128.4 (2C), 128.5, 128.7, 129.3, 135.7, 136.6, 155.2,

Example 21

Synthesis of (5S)-6-phenyl-5-[(tert-butyloxycarbonyl)-amino]-4-oxo-hexanoyl-L-proline N-ACE (11a)

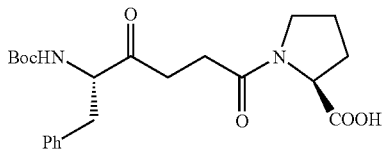

To a stirred solution of the benzyl ester 10 (100 mg, 0.1968 mmol) in dry EtOAc-MeOH (3:1 ratio) (10 mL) was added 10% Pd/C (50 mg) and the resulting mixture stirred at room temperature under 1 atmosphere of hydrogen for 24 h. Filtration of the black Pd residue and evaporation of the filtrate gave a crude residue. Column chromatography on silica gel elution with 20% MeOH-EtOAc afforded (5S)-6-phenyl-5-[(tert-butyloxycarbonyl)-amino]-4-oxo-hexanoyl-L-proline 11a as a pale colourless oil (74 mg, 90%); $R_f$ 0.23 (20% MeOH-EtOAc); IR (liquid film) ν 1720 (CO), 3000 (broad, COOH) cm$^{-1}$; $^1$H NMR (300 MHz, CDCl$_3$) $\delta_H$ 1.39 (9H, s, (CH$_3$)$_3$), 2.04 (2H, m, —CH$_2$—), 2.44 (1H, br-s, —COOH), 2.62 (4H, m,), 2.94 (3H, m), 3.16 (1H, m), 3.60 (2H, m, —CH$_2$N—), 4.52 (2H, m, 2×—CH—), 5.08 (1H, m, —NH—) and 7.14-7.35 (5H, m, Ar—H); $^{13}$C NMR (75 MHz, CDCl$_3$) $\delta_C$ 21.0, 22.6, 24.7, 28.0, 29.2, 30.9, 31.4, 34.6, 46.9, 58.7, 60.4, 126.8, 127.0, 128.5, 128.7, 129.5, 136.4, 155.3, 171.8, 173.7, 207.5 and 208.0; HRMS m/z calcd for C$_{22}$H$_{30}$N$_2$O$_6$ (M$^+$) 418.21734, found 418.21039.

Example 22

Synthesis of 5S)-5-[(N-benzoyl)amino]-4-oxo-6-phenyl-hexanoyl-L-proline (5a)

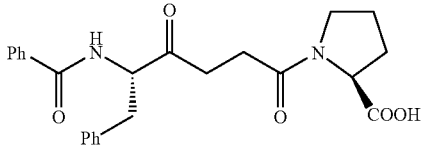

A solution of benzyl ester compound 10 (100 mg, 0.1968 mmol, 1.0 eq.) was dissolved in dry CH$_2$Cl$_2$ (10 mL) and cooled in an ice-water bath. 0.5M solution Trifluoroacetic acid (3.0 mL) was added dropwise and the resulting mixture stirred for 1 h. The mixture was allowed to warm-up to room temperature and stirred for a further 1 h. The resulting mixture was wash sequentially with 10% NaHCO$_3$ (10 mL), H$_2$O (10 mL), brine (10 mL) and dried the organic extract was dried over anhydrous MgSO$_4$ and evaporation of the solvent afforded a crude. To the crude mixture was added pyridine (5.0 mL) and cooled in an ice-water bath and then benzoyl chloride (0.1 mL, 0.862 mmol) was added. The mixture was stirred for 1 h at this temperature and a further 24 h at room temperature. The yellow solution was evaporated and then purified by column chromatography on silica gel elution with 50% EtOAc-hexane afforded (5S)-5-[(N-benzoyl)amino]-4-oxo-6-phenyl-hexanoyl-L-proline benzyl ester as a pale yellow viscous oil which foams in 85% yield. $^1$H NMR was identical. Hydrogenolysis of this benzyl ester with 10% Pd/C (50 mg) and dry EtOAc-MeOH (3:1 ratio) (10 mL) for 48 h afforded the compound 5a in 90% yield. $^1$H NMR was identical as previously reported.

Example 23

Synthesis of (5S)-6-phenyl-5-[(tert-butyloxycarbonyl)-amino]-4-oxo-hexanoyl-L-tryptophan methyl ester (NACE 118)

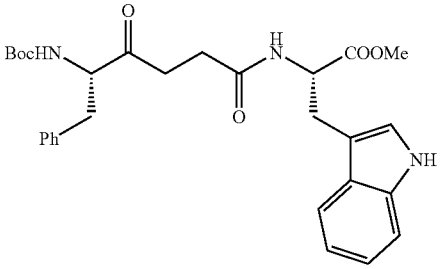

The experimental procedure employed for the synthesis of (5S)-6-phenyl-5-[(tert-butyloxycarbonyl)-amino]-4-oxo-hexanoyl-L-proline benzyl ester was followed using the free acid compound 9 (98 mg, 0.3054 mmol, 1.0 eq.), L-tryptophan methyl ester (67 mg, 0.3054 mmol, 1.0 eq.), 1-Hydroxybenzotriazole hydrate (HOBt) (42 mg, 0.3054 mmol, 1.0 eq.), N-ethyl-IV-(dimethylaminopropyl)-carbodiimide hydrochloride (EDC.HCl) (59 mg, 0.3054 mmol, 1.0 eq.), iPr$_2$NEt (0.055 mL, 0.3054 mmol, 1.0 eq.) and dry DMF/CH$_2$Cl$_2$ (2:8 ratio)(5 mL). Work-up as usual and column chromatography on silica gel elution with 50% EtOAc-hexane afforded the (5S)-6-phenyl-5-[(tert-butyloxycarbonyl)-amino]-4-oxo-hexanoyl-L-tryptophan methyl ester (NACE 118) as a cream white solid (0.129 g, 81%): mp 54-57° C.; $R_f$ 0.34 (50% EtOAc-hexane); IR (KBr) ν 1680 (CO) and 3000 (broad, NH) cm$^{-1}$; $^1$H NMR (400 MHz, CDCl$_3$) $\delta_H$ 1.40 (9H, s, (CH$_3$)$_3$), 2.41 (2H, t, J=6.6 Hz, —CH$_2$CO), 2.74 (2H, m, —CH$_2$CO), 2.88 (1H, m, —CH$_\alpha$Ph), 3.10 (1H, m, —CH$_\beta$Ph), 3.30 (2H, m, —CH$_2$Trp), 3.68 (3H, s, OCH$_3$), 4.47 (1H, br s, —NH), 4.89 (1H, dd, J=5.5 and 11.0 Hz, —CH—), 5.03 (1H, m, —CH—), 6.07 (1H, d, J=7.3 Hz, —NH), 7.08-7.58 (10H, m, Ar—H) and 8.15 (1H, br s, —NH-indole); $^{13}$C NMR (100 MHz, CDCl$_3$) $\delta_C$ 27.5, 28.3, 30.8, 35.4, 37.5, 52.3, 52.9, 53.0, 60.1, 111.2, 118.5, 119.7, 122.2, 122.9, 123.0, 126.9, 127.7, 128.6, 129.2, 129.3, 136.1, 136.3, 136.4, 155.4, 172.2, 172.3 and 204.6; EI-MS m/z calcd for C$_{29}$H$_{35}$N$_3$O$_6$ (M$^+$) 521.2526, found 521 (M$^+$).

Example 24

Synthesis of (5S)-6-phenyl-5-[(tert-butyloxycarbonyl)-amino]-4-oxo-hexanoyl-L-phenylalanine methyl ester (NACE 119)

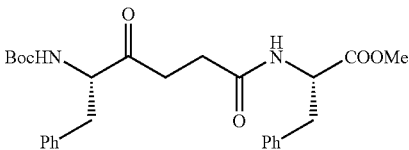

The experimental procedure employed for the synthesis of (5S)-6-phenyl-5-[(tert-butyloxycarbonyl)-amino]-4-oxo-hexanoyl-L-proline benzyl ester was followed using the free acid compound 9 (98 mg, 0.3054 mmol, 1.0 eq.), L-phenylalanine methyl ester hydrochloride (55 mg, 0.3054 mmol, 1.0 eq.), 1-Hydroxybenzotriazole hydrate (HOBt) (42 mg, 0.3054 mmol, 1.0 eq.), N-ethyl-N'-(dimethylaminopropyl)-carbodiimide hydrochloride (EDC.HCl) (59 mg, 0.3054 mmol, 1.0 eq.), iPr$_2$NEt (0.11 mL, 0.6110 mmol, 2.0 eq.) and dry DMF/CH$_2$Cl$_2$ (2:8 ratio)(5 mL). Work-up as usual and column chromatography on silica gel elution with 33% EtOAc-hexane afforded the (5S)-6-phenyl-5-[(tert-butyloxycarbonyl)-amino]-4-oxo-hexanoyl-L-phenylalanine methyl ester (NACE 119) as a pale viscous oil (0.140 g, 95%); R$_f$ 0.35 (40% EtOAc-hexane); IR (liquid film) v 1645 (CO) and 3170 (broad, NH) cm$^{-1}$; $^1$H NMR (400 MHz, CDCl$_3$) δ$_H$ 1.39 (9H, s, (CH$_3$)$_3$), 2.44 (2H, t, J=6.2 Hz, —CH$_2$CO), 2.77 (2H, m, —CH$_2$CO), 2.91 (1H, dd, J=6.6 and 13.2 Hz, —CH$_\alpha$Ph), 3.00-3.15 (3H, m, —CH$_\beta$Ph and —CH$_2$Ph), 3.71 (3H, s, OCH$_3$), 4.49 (1H, m, —CH—), 4.84 (1H, m, —CH—), 5.07 (1H, d, J=7.0 Hz, —NH), 6.03 (1H, d, J=7.7 Hz, —NH) and 7.08-7.58 (10H, m, Ar—H); $^{13}$C NMR (100 MHz, CDCl$_3$) δ$_C$ 28.2, 29.3, 29.4, 37.8 (2C), 52.2, 53.2, 60.3, 64.8, 126.9 (2C), 127.0, 127.1, 128.4, 128.5, 128.6, 129.2, 129.3, 129.5, 135.8, 136.4, 158.3, 171.9, 172.0 and 206.7; EI-MS m/z calcd for C$_{27}$H$_{34}$N$_2$O$_6$ (M$^+$) 482.2417, found 482 (M$^+$).

Example 25

Synthesis of (5S)-6-phenyl-5-[(tert-butyloxycarbonyl)-amino]-4-oxo-hexanoyl-L-tryptophan (11b)$^\pm$

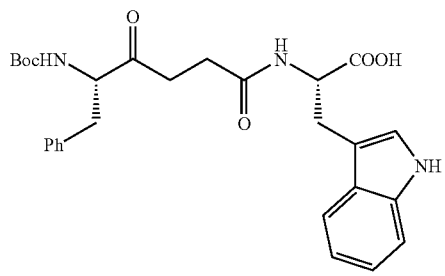

To a stirred solution of the compound (5S)-6-phenyl-5-[(tert-butyloxycarbonyl)-amino]-4-oxo-hexanoyl-L-tryptophan methyl ester (NACE 118) (100 mg, 0.1917 mmol, 1.0 eq.) in a mixture THF-MeOH (ratio 3:1) (5 mL) was added 0.5N LiOH (3.0 mL). The resulting yellowish mixture was stirred at room temperature for 5 h during which TLC shows the complete disappearance of the starting material. The reaction mixture was then neutralized with glacial acetic acid and the extracted with EtOAc (3×10 mL), dried over anhydrous MgSO$_4$ and evaporation of the solvent gave a crude residue, which was subjected to column chromatography on silica gel elution with 32% MeOH-EtOAc afforded the free acid Synthesis of (5S)-6-phenyl-5-[(tert-butyloxycarbonyl)-amino]-4-oxo-hexanoyl-L-tryptophan 11b as a pale yellow solid (88 mg, 91%); mp 141-143° C.; R$_f$ 0.43 (20% MeOH-EtOAc); IR (KBr) v 1665 (CO) and 3230 (broad, COOH/NH) cm$^{-1}$; $^1$H NMR (400 MHz, CD$_3$OD) δ$_H$ 1.34 (9H, s, (CH$_3$)$_3$), 2.38 (2H, t, J=6.6 Hz, —CH$_2$CO), 2.70 (3H, m, —CH$_2$CO and —CH$_\alpha$Ph), 3.06 (1H, dd, J=4.4 and 14.3 Hz, —CH$_\beta$Ph), 3.15 (2H, dd, J=7.2 and 14.7 Hz, —CH$_\alpha$Trp), 3.36 (2H, dd, J=4.7 and 14.7 Hz, —CH$_\beta$Trp), 4.28 (1H, m, —CH—), 4.56 (1H, q, J=6.0 Hz, —CH—) and 6.90-7.58 (10H, m, Ar—H); $^{13}$C NMR (100 MHz, CD$_3$OD) δ$_C$ 28.7 (2C), 30.5, 35.7, 37.4, 56.8 (2C), 62.3, 111.9, 112.2, 119.6, 119.7, 122.2, 124.4, 127.6, 129.3, 129.4, 130.3 (2C), 133.5, 137.9, 138.2, 154.4, 171.9, 172.0 and 206.2; EI-MS m/z calcd for C$_{28}$H$_{33}$N$_3$O$_6$ (M$^+$) 507.2369, found 507 (M$^+$). [$^\pm$ The carboxylic acid and amide protons were not observed, presumably, due to rapid exchange with water in the deuteriated NMR solvent.]

Example 26

Synthesis of (5S)-6-phenyl-5-[(tert-butyloxycarbonyl)-amino]-4-oxo-hexanoyl-L-phenylalanine (11c)$^\pm$

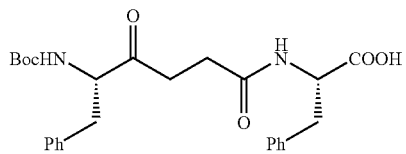

To a stirred solution of the compound (5S)-6-phenyl-5-[(tert-butyloxycarbonyl)-amino]-4-oxo-hexanoyl-L-phenylalanine methyl ester (NACE 119) (50 mg, 0.1036 mmol, 1.0 eq.) in a mixture THF-MeOH (ratio 3:1) (3.0 mL) was added 0.5N LiOH (2.0 mL). The resulting yellowish mixture was stirred at room temperature for 5 h during which TLC shows the complete disappearance of the starting material. The reaction mixture was then neutralized with glacial acetic acid and the extracted with EtOAc (3×10 mL), dried over anhydrous MgSO$_4$ and evaporation of the solvent gave a crude residue, which was subjected to column chromatography on silica gel elution with 20% MeOH-EtOAc afforded the free acid synthesis of (5S)-6-phenyl-5-[(tert-butyloxycarbonyl)-amino]-4-oxo-hexanoyl-L-phenylalanine 11c as a cream white viscous oil (40 mg, 83%); R$_f$ 0.48 (20% MeOH-EtOAc); IR (liquid film) v 1710 (CO) and 3240 (broad, COOH/NH) cm$^{-1}$; $^1$H NMR (400 MHz, CD$_3$OD) δ$_H$ 1.36 (9H, s, (CH$_3$)$_3$), 2.41 (2H, t, J=7.0 Hz, —CH$_2$CO), 2.69-2.77 (3H, m, —CH$_2$CO and —CH$_\alpha$Ph), 2.95 (1H, dd, J=7.7 and 14.0 Hz, —CH$_\beta$Ph), 3.09 (1H, m, —CH$_\alpha$Ph), 3.20 (1H, dd, J=4.8 and 13.6 Hz, —CH$_\beta$Ph), 4.26 (1H, m, —CH—), 4.59 (1H, q, J=6.6 Hz, —CH—) and 7.10-7.31 (10H, m, Ar—H); $^{13}$C NMR (100 MHz, CD$_3$OD) δ$_C$ 28.7, 29.1, 30.9, 32.3, 35.2, 57.9, 63.2, 63.4, 125.9, 126.2, 126.7, 127.1, 128.0, 129.3 (2C), 129.5, 129.7, 133.2, 135.8, 136.4, 157.4, 171.6, 173.4 and 204.2; EI-MS m/z calcd for C$_{26}$H$_{32}$N$_2$O$_6$ (M$^+$) 468.2260, found 468 (M$^+$). [$^\pm$ The carboxylic acid and amide protons were not observed, presumably, due to rapid exchange with water in the deuteriated NMR solvent.]

Example 27

Ace Inhibitory Activity

The ACE inhibitory activity (as tabulated in Table 1) was measured by the fluorometric determination of phthaldialdehyde-derivatised histidylleucine, a product of the enzyme reaction according to the method of Almquist et al.,[12] with some modifications. For tACEdelta36NJ and N-domain inhibition using Z-Phe-His-Leu as substrate:—10 µL of 0.05 mg/mL enzyme+120 µL inhibitor was incubated at ambient temperature for 3 hours. Inhibitor concentrations ranged from 2.0 µM to 500 µM. A 3.0 µL aliquot of this was assayed for enzyme activity using 30 µL of 1.0 mM Hip-His-Leu. This was incubated (in triplicate) for 30 mins at 37° C. and stopped with 180 µL solution of 0.28N NaOH. To this alkalized mixture 12 µL of o-phthaldialdehyde (150 mM) was added and the mixture incubated for another 10 mins at room temperature. Reactions were stopped by adding 26 µL of 3N HCl. Fluorescence was measured at Ex=360 nm; Em=486 nm, 5×5 slit width along with a His-Leu standard calibration curve fluorometer: Varian Cary Eclipse plate reader.

All assays included enzyme incubated with buffer in the absence of inhibitor (i.e. 0 µM inhibitor concentration). Lisinopril was also used as a positive control. The 50% inhibition ($IC_{50}$) of ACE activity was calculated as the concentrations of samples that inhibited 50% of ACE activity under these conditions.

than tACE (C domain). The tryptophan 5b derivative of keto-ACE highly C-domain specific (245-fold) and its inhibition potential is similar to that of keto-ACE 5a. The weaker ACE inhibitory activity of compounds 5a-c compared with lisinopril might be due to the absence of the $P_1'$ residue.

Example 28

Modeling Studies of keto-ACE and Analogues

Molecular modeling calculations were performed using the DISCOVER module of INSIGHT II (Accelrys Inc., Ver-

TABLE 1

ACE inhibition of the keto-ACE derivatives prepared above

| Compound | Structure | $K_i$ (tACE) ZPHL | $K_i$ (N-dom) ZPHL |
|---|---|---|---|
| Lisinopril | 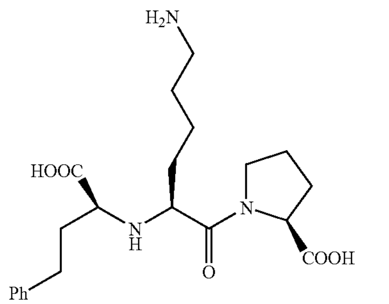 | 51.0 nM | 131.5 nM |
| 11a | 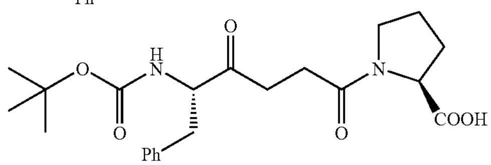 | 143.5 µM | 33.6 µM |
| 5a | 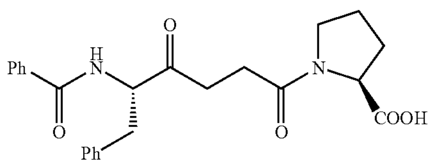 | 1.8 µM | 45.2 µM |
| 5b | 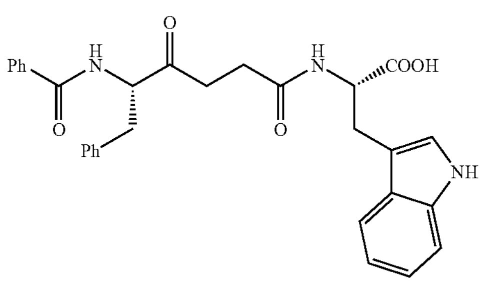 | 0.8 µM | 195.7 µM |
| 5c | 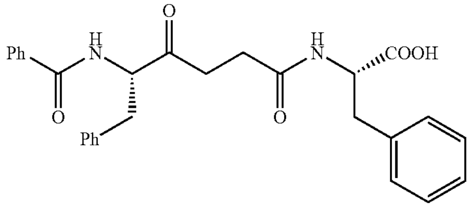 | 23.7 µM | 84.3 µM |

Keto-ACE 5a and analogues 5b, 5c and compound 11a all showed weak inhibitory activity for ACE as compared to lisinopril. Compound 11a inhibits N-domain more effectively sion 98.0) on a Silicon Graphics Octane 1 workstation. The starting structure was the X-ray crystal structure of testis ACE complexed with the known inhibitor lisinopril.[11] After removing the crystallographic water molecules and adding hydrogens, the CVFF and the ESFF (metal adapted) forcefields[25] were used in all energy minimizations and dynamic runs. The conjugate gradient minimization algorithm was used after running 1000 initial steps, and then 3000 cycles of molecular dynamics followed by 3000 cycles of energy minimization in an NTV ensemble, at a temperature of 300K. All calculations were carried out in a dielectric constant of 1.00 and a cut-off distance of 9.50 Å. The structures of the keto-ACE 5a and analogues 5b and 5c were generated with standard bond lengths and angles using the builder tool of INSIGHT II software (Accelrys Inc.) and then minimized. The initial position of the compounds in the active site of the catalytic C-domain of ACE was obtained by superimposing the important pharmacophoric groups of keto-ACE and analogues on the corresponding atoms of lisinopril in the tACE-lisinopril complex. After removal of the reference inhibitor (lisinopril), the structure of the inhibitor-complex was refined by running energy minimizations and molecular dynamics.

Figure 2:
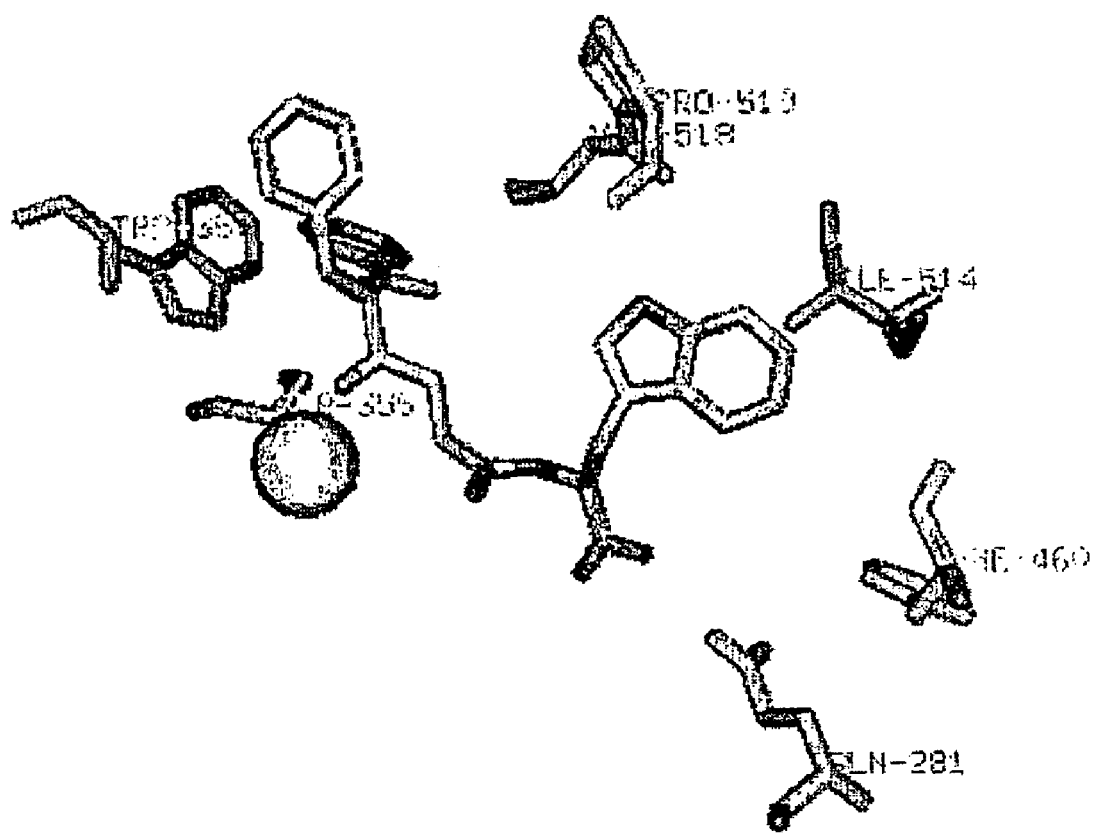
FIG. 2 shows the interactions between the benzoyl and tryptophan moieties of compound 5b with some active site residues in the $S_1$ and $S_2'$ subsites of ACE (in cyan color). The active site Zn atom is shown in magenta color.

The compounds Keto-ACE 5a and analogues 5b and 5c, which presented the highest C-domain selectivity, were modeled into the testis ACE binding site occupying the $S_1$, $S_2$ and $S_2'$ subsites (FIG. 1). From the docking experiments, the energy-minimized bound conformer of the inhibitors in the active site of the C-domain was obtained. The inhibitors all exhibited a negative total potential energy of the protein-ligand interaction ($-835.4$ Kcal mol$^{-1}$, $-933.9$ Kcal mol$^{-1}$, and $-799.0$ Kcal mol$^{-1}$ for 5a, 5b and 5c, respectively) which is an indication of the relative stability of the enzyme-ligand complex, (the value for t ACE-lisinopril complex was also found to be $-890.0$ Kcal mol$^{-1}$). The residues forming the subsites of the C-domain active site were defined as those located at a distance less than 6.00 Å from the important functionalities of inhibitors. The modeling of compound 5b revealed that the phenyl group of the $P_1$ phenylalanine interacted with the hydrophobic Val518 [Val1094 in somatic enzyme][26] and the polar Ser355 (Ser931) of the $S_1$ subsite at distances of 2.87 Å and 4.30 Å, respectively. The distance between the phenylalanine-carbonyl and the Zn-atom in the active site of the C-domain was observed to be 2.82 Å for compound 5b (and 2.79 Å and 3.00 Å for compounds 5a and 5c, respectively). These values are within the range of a reasonable H-bonding interaction. Also, the modeling of compound 5b showed that the $P_2$ phenyl group of the benzoyl moiety was accommodated into the $S_2$ subsite and this interacted with residues Ser355 (Ser931), Trp357 (Trp933), Lys368 (Lys944) Asn66 (Asn642), Asn70 (Asn646), Glu143 (Glu719), Phe512 (Phe1088), and Ser516 (Ser1092) (FIG. 2).

In the N-domain, Asn66 (Asn642), Asn70 (Asn646), Glu143 (Glu719), and Ser516 (Ser1092) are replaced by a Ser39, an Asp43, a Ser119, and a Asn494, respectively. Thus, these interactions might likely contribute to the domain-selectivity of the compounds 5b and 5a. The $S_2'$ subsite readily accommodated the tryptophan and the phenylalanine moieties of compounds 5b and 5c, respectively. The tryptophan moiety of compound 5b made contacts with Gln281 (Gln857), Phe460 (Phe1036), Ile 514 (Ile1090), Val518 (Val1094), and Pro 519 (Pro1095) residues (FIG. 2). In the N-domain of ACE, the Ile514 (Ile1090) and Val518 (Val1094) are replaced by Val492 and Thr496, respectively, while the other residues are not conserved in the N- and C-domains. These interactions might result in a contribution to domain-selectivity on the one hand and also loss of potency on the other.

Molecular docking of the energy-minimized conformers of compounds 5a, 5b, and 5c in the tACE active site showed that the selectivity of these compounds may be explained by the interactions involving the $S_1$, $S_2$, and $S_2'$ subsites. The bulky aromatic ring of the $P_1$ Phe of compound 5b extended into the deep $S_1$ pocket (FIG. 2). Of the residues that made contact with the $P_1$ residue, Val518 (Val1094) and Phe391 (Phe967) are both replaced by the polar Thr496 and Tyr369 in the N-domain respectively. These substitutions increase the hydrophilicity of the $S_1$ pocket which would be less favourable for binding a $P_1$ phenylalanine and does not fit with the general picture that a phenyl group at this position has been shown to be significant for ACE inhibitory activity. Instead, it would likely cause steric hindrance.

From the docking results, the benzoyl group is accommodated into the $S_2$ subsite, which is in agreement with the ACE inhibitory activity observed for compounds 5a, 5b, and 5c. Among the residues that made contact with the benzoyl group of compound 5b, four are conserved between the C- and N-domains. In the C-domain of ACE, the polar residues Asn66 (Asn642), Asn70 (Asn646), Glu143 (Glu719), and Ser516 (Ser1092) residues are replaced by polar residues Ser39, Asp43, Ser119, and Asn494 in the N-domain, respectively. However, Ser39 in the N-domain is less polar than Asn66 (Asn642) in the C-domain, since amide groups are known to be more polar than hydroxyl groups. Also, Asp43, Ser119, and Asn494 in the N-domain are more polar than their counterparts in the C-domain. These differences in polarity between the groups could favour more interactions with less-polar inhibitor side chains and decrease the affinity for the N-domain, and as such result in the increase in selectivity of compound 5b.

The $S_2'$ subsites of both the C- and N-domains are relatively large and can accommodate various linear and cyclic side chains without stringent preferences. It has been reported previously[27,28] that the selectivity of ACE inhibitors depends on the interactions with the $S_2'$ pocket. The less polar tACE Ile514 (Ile1090) and Val518 (Val1094) residues in the $S_2'$ pocket are replaced by the more polar Val492 and Thr496 residues in the N-domain. Ile514 and Val518 of the C-domain display a greater hydrophobic interaction with the bulky tryptophan moiety of compound 5b. It has recently been shown by Dive and co-workers[27] that the $S_2'$ subsite can easily accommodate a tryptophan moiety, increasing C-domain selectivity. The molecular modeling results for compound 5b also revealed extra H-bondings between the indole-NH of the tryptophan moiety with Val 518 and Pro 519 of the active site, at distances of 2.43 Å and 2.73 Å, respectively.

The higher $K_I$ observed for compound 11a might be due to the tertiary-butyl group not fitting into the $S_2$ subsite. Compound 5b showed significant ACE inhibitory potency, which might be a result of the tryptophan moiety at this position interacting with the hydrophobic $S_2$ subsite of the enzyme through its imidazole nucleus. (Bala et al. have previously reported that a tryptophan moiety at the $S_2'$ position enhances ACE inhibitory activity).[29] The free carboxylic group of the tryptophan residue interacted with the amino groups of the side chains of the Lys511 and Gln281 residues in the active site of tACE, at H-bonding distances of 1.71 Å and 1.90 Å, respectively.

The applicant has thus developed a novel and straightforward process for the synthesis of keto-ACE and analogues thereof. The key feature of this synthesis involves a Horner-Emmons[24] olefination of the α,β-unsaturated keto-phosphonate with ethyl glyoxylate. The keto-ACE analogues display C-domain selectivity and their interactions with tACE were studied by a molecular modeling approach.

REFERENCES

1. Skeggs, L. T.; Kahn, J. R. and Shumway, N. P. (1956) The preparation and function of the hypertension-converting enzyme, *J. Exp. Med.* 103, 295-299.

2. Erdös, E. G. (1976) Conversion of angiotensin I to angiotensin II, *Am. J. Med.* 60, 749-759.
3. Peach, M. J. (1977) Renin-angiotensin system: Biochemistry and mechanism of action, *Physiol. Rev.* 57, 313-370.
4. Ehlers, M. R. W and Riordan, J. F. (1989) Angiotensin-converting enzyme: New concepts concerning its biological role, *Biochemistry*, 28, 5312-5318.
5. Cushman, D. W.; Cheung, H. S.; Sbo, E. F. and Ondetti, M. A. (1977) Design of potent competitive inhibitors of angiotensin-converting enzyme. Carboxyalkanoyl and mercaptoalkanoyl amino acids, *Biochemistry*, 16, 5484-5491.
6. Ondetti, M. A.; Rubin, B. and Cushman, D. W. (1977) Design of specific inhibitors of angiotensin-converting enzyme: New class of orally active antihypertensive agents, *Science*, 196, 441-444.
7. Brown, N. J. and Vaughan, D. E. (1998) Angiotensin-converting enzyme inhibitors, *Circulation*, 97(14), 1411-1420.
8. Raia, Jr. J. J.; Barone, J. A.; Byerly, W. G. and Lacy, C. R. (1990) Angiotensin-converting enzyme inhibitors: A comparative review, *DICP*, 24(5), 506-525.
9. Antonios, T. F. and MacGregor, G. A. (1995) Angiotensin-converting enzyme inhibitors in hypertension: Potential problems, *J. Hypertens. Suppl.*, 13(Suppl), S11-S16.
10. Israili, Z. H. and Hall, W. D. (1992) Cough and angioneurotic edema associated with angiotensin-converting enzyme inhibitor therapy: A review of the literature and pathophysiology, *Annals in Internal Medicine*, 117, 234-242.
11. Natesh, R.; Schwager, S. L. U.; Sturrock, E. D. and Acharya, K. R. (2003) Crystal structure of the human angiotensin-converting enzyme-lisinopril complex, *Nature*, 421, 551-554.
12. Almquist, R. G.; Chao, W.-R.; Ellis, M. E. and Johnson, H. L. (1980) Synthesis and biological activity of a ketomethylene analogue of a tripeptide inhibitor of angiotensin-converting enzyme, *J. Med. Chem.*, 23, 1392-1398.
13. Meyer, R. F.; Nicolaides, E. D.:; Tinney, F. J.; Lunney, E. A.; Holmes, A.; Hoefle, M. L.; Smith, R. D.: Essenburg, A. D.; Kaplan, H. R. and Almquist, R. G. (1981) Novel synthesis of (S)-1-[5-(benzoylamino)-1,4-dioxo-6-phenyl-hexyl]-L-proline and analogues: Potent angiotensin-converting enzyme inhibitors, *J. Med. Chem.*, 24, 964-969.
14. (a) Almquist, R. G.; Crase, J.; Jennings-White, C.; Meyer, R. F.; Hoefle, M. L.; Smith, R. D.; Essenburg, A. D. and Kaplan, H. R. (1982) Derivatives of the potent angiotensin-converting enzyme Inhibitors 5(S)benzamido-4-oxo-6-phenylhexanoyl-L-proline: Effect of changes at positions 2 and 5 of the hexanoic acid portion, *J. Med. Chem.*, 25, 1292-1299. (b) Deddish, P. A.; Marcic, B.; Jackmann, H. L.; Wang, H. Z.; Skidgel, R. A. and Erdös, E. G. (1998) N-domain-specific substrate and C-domain inhibitors of angiotensin-converting enzyme: Angiotensin-(1-7) and Keto-ACE, *Hypertension*, 31, 912-917.
15. González-Muñiz, R.; García-López, M. T.; Gómez-Monterrey, I.; Herranz, R.; Jimeno, M. L.; Suárez-Gea, M. L; Johansen, N. L.; Madsen, K.; Thøgersen, H.; and Suzdak, P. (1995) Ketomethylene and (Cyanomethylene) amino pseudopeptide analogues of the C-terminal hexapeptide of neurotensin, *J. Med. Chem.*, 38, 1015-1021 and references cited therein.
16. Dézil, R.; Plante, R.; Caron, V.; Grenier, L.; Ulnas-Brunet, M.; Duceppe, J.-S.; Malenfant, E. and Moss, N. (1996) A practical and diastereoselective synthesis of Ketomethylene dipeptide Isosteres of the type AAψ(COCH$_2$)Asp, *J. Org. Chem.*, 61, 2901-2903.
17. Benedetti, F.; Miertus, S.; Norbedo, S.; Tossi, A. and Ziatoidzky, P. (1997) Versatile and stereoselective synthesis of diamino diol dipeptide isosteres: Core units of pseudopeptide HIV protease inhibitors, *J. Org. Chem.*, 62, 9348-9353.
18. Ghosh, A. K. and Fidanze, S. (1998) Transition-state mimetics for HIV protease inhibitors: Stereocontrolled synthesis of hydroxyethylene and hydroxyethylamine isosteres by ester-derived titanium enolate syn and anti-diol reactions, *J. Org. Chem.*, 63, 6146-6152.
19. Benedetti, F.; Maman, P. and Norbedo, S. (2000) New synthesis of 5-amino-4-hydroxy-2,6-dimethylheptanoic acid: A hydroxyethylene isostere of the Val-Ala dipeptide, *Tetrahedron Lett.*, 41, 10075-10078.
20. Benedetti, F.; Magnan, M.; Miertus, S.; Norbedo, S.; Parat, D. and Tossi, A. (1999) Stereoselective synthesis of non symmetric dihydroxyethylene dipeptide isosteres via epoxyalcohols derived from α-amino acids, *Bioorg. Med. Chem. Lett.*, 9, 3027-3030.
21. Tossi, A.; Benedetti, F.; Norbedo, S.; Skrbec, D.; Berti, F. and Romeo, D. (2003) Small hydroxyethylene-based peptidomimetics inhibiting both HIV-1 and *C. albicans* aspartic proteases, *Bioorg. Med. Chem.*, 11, 4719-4727.
22. García-López, M. T.; González-Muñiz, R. and Harto, J. R. (1988) A simple and versatile route to ketomethylene dipeptide analogues, *Tetrahedron Lett.*, 29, 1577-1580.
23. García-López, M. T.; González-Muñiz, R. and Harto, J. R. (1988) Synthesis of ketomethylene dipeptides containing basic amino acid analogues at C-terminus, *Tetrahedron*, 44, 5131-5138.
24. Kelly, T. R.; Schmidt, T. E. and Haggerty, J. G. (1972) A convenient preparation of methyl and ethyl glyoxylate, *Synthesis*, 544-545.
25. http://www.accelrys.com/support/lifeldiscovertforcefield/esffSBL.html
26. Soubrier, F.; Alhenc-Gelas, F.; Hubert, C.; Allegrini, J.; John, M.; Tregear, G. and Corvol, P. (1988) Two putative active centers in human angiotensin l-converting enzyme revealed by molecular cloning, *Proc. Natl. Acad. Sci. U.S.A.* 85, 9386-9390.
27. Georgiadis, D.; Cuniasse, P.; Cotton, J.; Yiotakis, A. and Dive, V. (2004) Structural determinants of RXPA380, a potent and highly selective Inhibitor of the angiotensin-converting enzyme C-domain, *Biochemistry*, 43, 8048-8054.
28. Bersanetti, P. A.; Andrade, M. C. C; Casarini, D. E.; Juliano, M. A.; Nchinda, A. T.; Sturrock, E. D.; Juliano, L. and Carmona, A. K. (2004) Positional-scanning combinatorial libraries of fluorescence resonance energy transfer (FRET) peptides to define substrate specificity of angiotensin I-converting enzyme and development of selective C-domain substrates, *Biochemistry*, accepted in press.
29. Bala, M.; Pasha, M. A. Q.; Bhardwaj, D. K. and Pasha, S. (2002) Novel Peptidomimics as Angiotensin-Converting Enzymes inhibitors: A combinatorial approach, *Bioorg. and Med. Chem.*, 10, 3685-3691.
30. Da, C.-S.; Han, Z.-J.; Ni, M.; Yang, F.; Liu, D.-X.; Zhou, Y.-F. and Wang, R. (2003) A convenient synthesis of piperidine-based β-amino alcohols from L-Phe and highly enantioselective addition of diethyl zinc to aldehydes, *Tetrahedron: Asymmetry*, 14, 659665.
31. (a) Hvidt, T. and Szarek, W. A (1988) Synthesis of enantiomerically pure β-amino-α-methylene-γ-butyrolactones by way of ozonolysis of aromatic α-amino acids, *Can. J. Chem.*, 66(4), 779782; (b) Peng, S. and Winterfeldt, E. (1990) Enantiomerically pure indoloquinolizines from tryptophane, *Liebigs Ann. Chem.*, 313-318.

The invention claimed is:
1. A compound of formula 5b:

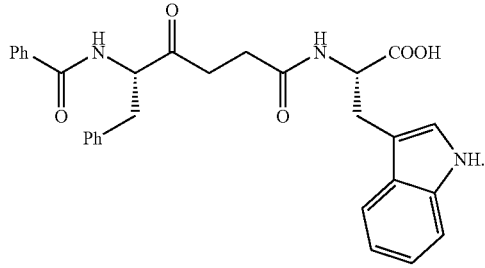

(5b)

2. A pharmaceutical composition comprising the compound according to claim 1, wherein said compound is present in an amount sufficient for treating hypertension and/or cardiovascular disease.

3. A method for treating hypertension and/or cardiovascular disease comprising administering to a patient in need thereof an effective amount of the compound according to claim 1.

* * * * *